US012693295B2

(12) United States Patent (10) Patent No.: US 12,693,295 B2
Zeng (45) Date of Patent: Jul. 28, 2026

(54) METHODS FOR INKJET PRINTING OBJECTS FOR MICROFLUIDIC DEVICES

(71) Applicant: University of Kansas, Lawrence, KS (US)

(72) Inventor: Yong Zeng, Gainesville, FL (US)

(73) Assignee: University of Kansas, Lawrence, KS (US)

( * ) Notice: Subject to any disclaimer, the term of this patent is extended or adjusted under 35 U.S.C. 154(b) by 998 days.

(21) Appl. No.: 17/791,079

(22) PCT Filed: Mar. 2, 2021

(86) PCT No.: PCT/US2021/020419
§ 371 (c)(1),
(2) Date: Jul. 6, 2022

(87) PCT Pub. No.: WO2021/178376
PCT Pub. Date: Sep. 10, 2021

(65) Prior Publication Data
US 2023/0024611 A1 Jan. 26, 2023

Related U.S. Application Data

(60) Provisional application No. 62/984,541, filed on Mar. 3, 2020.

(51) Int. Cl.
*G01N 33/575* (2026.01)
*C12Q 1/37* (2006.01)
(Continued)

(52) U.S. Cl.
CPC ........... *G01N 33/5758* (2026.01); *C12Q 1/37* (2013.01); *G01N 21/6428* (2013.01);
(Continued)

(58) Field of Classification Search
CPC ......... G01N 33/57484; G01N 21/6428; G01N 21/6456; G01N 33/54386; G01N 33/6872;
(Continued)

(56) References Cited

U.S. PATENT DOCUMENTS 6,509,085 B1 * 1/2003 Kennedy ............. B81C 1/00119
428/206
10,294,567 B2 * 5/2019 Ma ....................... C23C 18/1893
(Continued)

FOREIGN PATENT DOCUMENTS

CN        104004652 A      8/2014

OTHER PUBLICATIONS

Sowade, Enrico et al. "Inkjet Printing of Colloidal Nanospheres: Engineering the Evaporation-Driven Self-Assembly Process to Form Defined Layer Morphologies." Nanoscale research letters vol. 10,1 (2015): 362. doi:10.1186/s11671-015-1065-2 (Year: 2015).*
(Continued)

*Primary Examiner* — Gregory S Emch
*Assistant Examiner* — McKenzie A Dunn
(74) *Attorney, Agent, or Firm* — Bell & Manning, LLC

(57) ABSTRACT

Provided herein are methods for inkjet printing objects, including objects which may be used as elements of microfluidic devices. The microfluidic devices incorporating the elements are also provided. Such microfluidic devices include those configured to quantify the expression and activity of exosomal matrix metalloprotease, MMP14. These microfluidic devices may be used in methods of monitoring breast cancer in patients having breast cancer.

14 Claims, 20 Drawing Sheets

(51) Int. Cl.
    *G01N 21/64*         (2006.01)
    *G01N 33/543*      (2006.01)
    *G01N 33/68*       (2006.01)

(52) U.S. Cl.
    CPC ... *G01N 21/6456* (2013.01); *G01N 33/54386*
        (2013.01); *G01N 33/6872* (2013.01); *G01N*
          *2021/6432* (2013.01); *G01N 2021/6439*
       (2013.01); *G01N 2333/70596* (2013.01); *G01N*
                   *2333/96494* (2013.01)

(58) Field of Classification Search
    CPC ... G01N 2021/6432; G01N 2021/6439; G01N
              2333/70596; G01N 2333/96494; G01N
             33/57415; G01N 33/54313; C12Q 1/37;
             B01L 2300/0636; B01L 2300/0816; B01L
             2300/0864; B01L 2300/0883; B01L
             2300/0887; B01L 3/502707
    See application file for complete search history.

(56) References Cited

U.S. PATENT DOCUMENTS

| | | |
|---|---|---|
| 2009/0097022 A1 | 4/2009 | Shen et al. |
| 2016/0229128 A1 | 8/2016 | Dayagi et al. |
| 2018/0229425 A1 | 8/2018 | Sheinman |

OTHER PUBLICATIONS

Daaboul, George G et al. "Digital Detection of Exosomes by Interferometric Imaging." Scientific reports vol. 6 37246. Nov. 17, 2016, doi:10.1038/srep37246 (Year: 2016).*

Peng Zhang et al., "Multiplexed immunophenotyping of circulating exosomes on nano-engineered ExoProfile chip towards early diagnosis of cancer," *Chem. Sci.*, 2019, vol. 10; pp. 5495-5504.

Peng Zhang et al., "Ultrasensitive detection of circulating exosomes with a 3D-nanopatterned microfluidic chip," *Nat Biomed Eng.* Jun. 2019, vol. 3, No. 6; pp. 438-451. DOI:10.1038/s41551-019-0356-9.

Hongmei Cao et al., "Microfluidic Exponential Rolling Circle Amplification for Sensitive microRNA Detection Directly from Biological Samples," *Sens Actuators B Chem.* Jan. 15, 2019, vol. 279; pp. 447-457. DOI: 10.1016/j.snb.2018.09.121.

Peng Zhang et al., "Molecular and functional extracellular vesicle analysis using nanopatterned microchips monitors tumor progression and metastasis," *Sci. Transl. Med.*, vol. 12, eaaz1278 Jun. 10, 2020, pp. 1-17.

Peng Zhang et al., Supplementary Materials for "Molecular and functional extracellular vesicle analysis using nanopatterned microchips monitors tumor progression and metastasis," *Sci. Transl. Med.*, vol. 12, eaaz1278 Jun. 10, 2020, pp. 1-17. DOI: 10.1126/scitranslmed. aaz2878.

The International Search Report and the Written Opinion issued on May 26, 2021 for international patent application No. PCT/US2021/020419; pp. 1-9.

* cited by examiner

Stacked coins printing

Inkjet printing an additional set of offset and partially overlapping rings on the second set A first set of offset and partially overlapping rings

1

Heating

3

2

A second set of offset and partially overlapping rings

Unmodified glass substrate

A 3D object composed of a stack of three sets of offset and partially overlapping rings

METHODS FOR INKJET PRINTING OBJECTS FOR MICROFLUIDIC DEVICES

CROSS-REFERENCE TO RELATED APPLICATIONS

The present application is a National Stage of International Application No. PCT/US21/20419, filed Mar. 2, 2021, which claims priority to U.S. provisional patent application No. 62/984,541 that was filed Mar. 3, 2020, the entire contents of both of which are incorporated herein by reference.

REFERENCE TO GOVERNMENT RIGHTS

This invention was made with government support under CA186846, CA214333, and CA207816 awarded by the National Institute of Health. The government has certain rights in the invention.

BACKGROUND

Microfluidic devices have been used as a platform for a variety of biosensing techniques, which generally rely on target species interacting with surface-immobilized probes for affinity capture. Standard soft photolithography is often used to form microfluidic devices. This involves the use of patterned molds to create various components of the devices, including silica elements positioned within the assay chambers of such devices. To form the silica elements, colloidal suspensions of silica are injected into the patterned molds and the silica elements form via self-assembly as the liquid of the colloid evaporates out of the patterned molds.

SUMMARY

Provided herein are methods for inkjet printing objects, including objects which may be used as elements of microfluidic devices. The microfluidic devices incorporating the elements are also provided. Such microfluidic devices include those configured to quantify the expression and activity of exosomal matrix metalloprotease, MMP14. These microfluidic devices may be used in methods of monitoring breast cancer in patients having breast cancer.

In one aspect, methods for inkjet printing an object are provided. In embodiments, such a method comprises depositing a first droplet of an ink composition comprising particles dispersed in a liquid phase onto a surface of a substrate at first location and evaporating the liquid phase from the deposited first droplet to form a first ring of the particles on the surface at the first location; depositing a second droplet of the ink composition onto the surface at a second location laterally offset from the first location by a droplet spacing value and evaporating the liquid phase from the deposited second droplet to form a second ring of the particles on the surface at the second location, the second ring offset from, and partially overlapping with, the first ring; and repeating step (b) one or more additional times with one or more additional droplets to form a first layer of offset and partially overlapping rings on the surface of the substrate, the first layer comprising the first and second rings and one or more additional rings formed from the one or more additional droplets, thereby forming an object.

In another aspect, microfluidic devices are provided. In embodiments, such a microfluidic device comprises an assay chamber comprising an inkjet printed object positioned therein, the inkjet printed object comprising a plurality of stacked layers, each layer comprising a plurality of rings, each ring comprising a plurality of particles, wherein adjacent rings in the plurality of rings are laterally offset from one another by a droplet spacing value and partially overlap with one another.

In another aspect, methods of diagnosing breast cancer are provided. In embodiments, such a method comprises obtaining a liquid biopsy from a patient having breast cancer; quantifying proteolytic activity of MMP14 in the liquid biopsy; and quantifying expression of MMP14 in the liquid biopsy.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

FIG. 1A shows the design of the EV-CLUE chip composed of a pneumatic control circuit and an array of eight parallel assay reactors patterned with 3D nanostructured colloidal microelements to enhance immunocapture of circulating sEVs. The pneumatically operated chip integrates three parallel sEV assays: (a1) MMP14 proteolytic activity assay using a specific FRET peptide probe and ELISA quantitation of (a2) sEV MMP14 protein expression and (a3) the total sEV concentration determined by CD63 and CD9. The eight-channel design allows parallel analysis of two samples, combined with the control assays with PBS blank (a4) to determine the background signal levels for both expression and activity assays. FIG. 1B demonstrates the "stacked coins" colloidal inkjet printing approach for fabrication of 3D self-assembled microelements on an untreated hydrophilic glass substrate. FIGS. 1C-1E show SEM images of various micropatterns composed of an array of (FIG. 1C) sinusoidal strips, (FIG. 1D) diamonds, and (FIG. 1E) X shapes, respectively, deposited by 15-cycle inkjet printing of 1 $\mu$m silica colloids.

FIG. 2A shows the comparison of sEV capture efficiency for standard ultra-centrifugation (UC) and the nanochips fabricated by the $\mu$cSA and colloidal ink-jet printing methods. Fluorescently stained EVs of various cancer cell lines were spiked in healthy plasma at $10^6$ $\mu L^{-1}$. FIG. 2B compares the flat-channel and nano-engineered chips for specific detection of MMP14 in UC-purified vesicles ($10^6$ $\mu L^{-1}$) from various breast cancer cell lines. Two-tailed Student's t-test was used for two-sample comparison with the significance level set at P<0.05. FIG. 2C shows the calibration of the EV-CLUE chip by measuring the total sEV concentration (determined by CD9 and CD63), MMP14 expression (MMP14-E), and MMP14 proteolytic activity (MMP14-A) of MDA-MB-231 EVs. Inset: Determination of LODs for the MMP14 activity assay from three standard deviations (S.D.) of the backgrounds (dashed lines). FIG. 2D shows the integrative multi-parameter analysis of purified EVs ($10^6$ $\mu L^{-1}$) from three breast cancer cell lines with different levels of invasiveness. Statistical difference was determined by one-way ANOVA with post-hoc Tukey's pairwise multiple comparisons test at the significance level of P<0.05. Anti-CD81 capture mAb was used in all cases. Error bars indicate one S.D. (n=3).

FIG. 3A shows the measurement of the expression of MMP14, MMP15 and MMP16 proteins on breast cancer-derived EVs. 100 μL purified EVs ($10^7$ μL$^{-1}$) from three cell lines and 20 μL patient plasma were assayed using the commercial microplate ELISA kits. The plasma sample was 1:5 diluted in PBS. Statistical analysis was conducted with one-way ANOVA with post-hoc Tukey's test at the significance level of P<0.05. FIG. 3E shows the correlation of the measured sEV MMP14 proteolytic activity with the number of invasive cells counted in the Matrigel assays. The linear fitting was performed using the Deming regression model at the 95% confidence level. In all cases, anti-CD81 mAb was used for sEV capture and each sample was measured in triplicate. Error bars: one S.D. (n=3).

FIG. 4A shows corresponding tumor intensity plots that were acquired for each mouse at three stages: I) prior to inoculation; II) initial detection of early metastasis; III) close to moribund with extensive lung metastases. FIGS. 4B-4D show multiplexed total sEV (CD9&CD63), MMP14-E and MMP14-A analyses of circulating sEVs directly in mouse plasma using the EV-CLUE technology. ~50 μL blood was collected from tail vein at each stage. 6 μL plasma was diluted in PBS by 5 times and analyzed on chip using the anti-human mAbs validated for specific detection of human tumor xenograft-derived sEVs. Each sample was assayed in triplicate to determine the mean and S.D. (error bars). P values were determined by one-way repeated measures ANOVA with post-hoc Tukey's pairwise multiple comparisons test at the significance level of P<0.05. FIG. 4E shows the correlation of the sEV MMP14 expression and activity measured for 10 xenografted mice at the Stage III with the tumor sizes measured by bioluminescent imaging. Error bars indicate S.D. (n=3). Deming linear fitting was performed at the 95% confidence level.

FIG. 5A shows the correlation between the sEV MMP14 expression and activity measured for all plasma samples in. FIG. 5B shows the time-lapse curves of the measurements of three sEV markers in the mice which developed primary tumor only (n=4) or with lung metastasis (n=12). Error bars: s.e.m. of each group. P values were determined by two-way ANOVA at the 95% confidence level. FIG. 5C shows the correlation of the sEV markers measured for 16 mice at Week 5 with the count of lung metastasis nodules. FIG. 5D shows the correlation of the sEV markers with the primary tumor volume measured from Week 2 to 5 for 4 mice which only developed primary tumors. Error bars indicate S.D. (n=3 technical repeats). Linear Deming fitting in FIGS. 5A, 5C, 5D was performed at the 95% confidence level.

FIG. 6A shows scatter plots of the sEV markers and SUM3 signature for detecting BrCa against the control. Non-parametric, two-tailed Mann-Whitney U-test were used for two-group comparison. FIG. 6B shows scatter plots of the sEV markers and SUM3 signature for differentiating individual groups at progressing disease stages. Kruskal-Wallis one-way ANOVA with post hoc Dunn's test for pairwise multiple comparisons was used to determine the overall and each group pair's P values. FIGS. 6C-6D show classification of the training cohort by discriminant analysis of the three-marker panel COM3 was summarized in the heat map of classification probabilities, confusion matrix (FIG. 6D), and canonical score plot of the first two canonical variables that together capture 99.93% of the variance (FIG. 6C). The middle line and error bar in FIGS. 6A and 6B represent the mean and one s.e.m., respectively. All statistical analyses were performed at 95% confidence level.

FIG. 7A shows evaluation of the sEV markers individually and in combinations for breast cancer diagnosis. Two-tailed Mann-Whitney U-test were used for two-group comparisons. FIG. 7B shows evaluation of the sEV markers and SUM3 signature for differentiating individual groups at progressing disease stages. Kruskal-Wallis one-way ANOVA with post hoc Dunn's test for pairwise multiple comparisons was used to determine the overall and each group pair's P values. FIGS. 7C-7D show multivariate classification to assess the combined three sEV markers for identifying the control and patient groups with pre-invasive, invasive and metastatic BrCa, as presented by the heat map of classification probabilities, confusion matrix (FIG. 7C, and canonical score plot of the first two canonical variables derived from the discriminant analysis of the training cohort (FIG. 7D). The middle line and error bar in FIGS. 7A and 7B represent the mean and one s.e.m., respectively. All statistical analyses were performed at 95% confidence level.

DETAILED DESCRIPTION

Figure 1A:
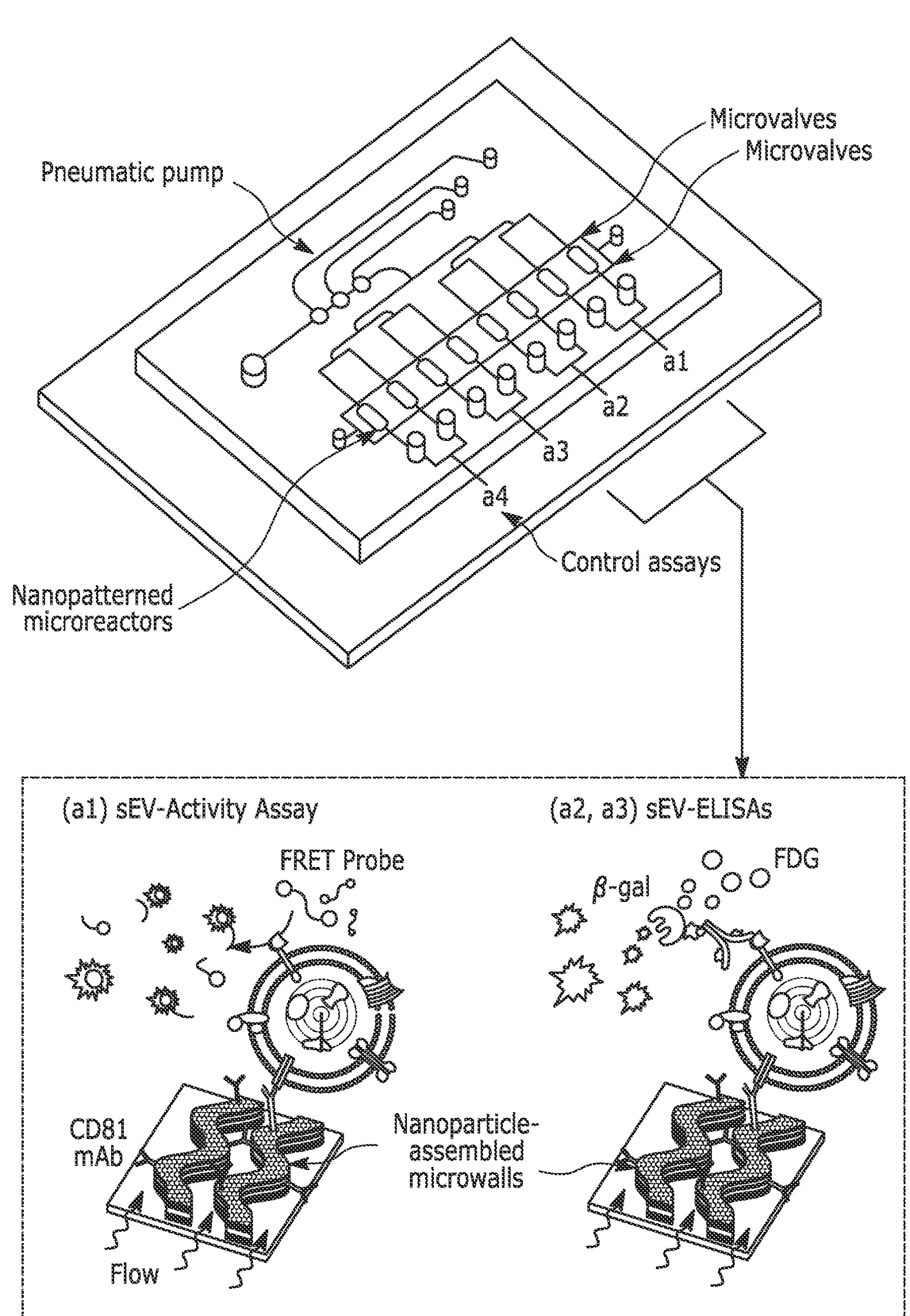
FIGS. 1A-1E demonstrate a nano-engineered EV-CLUE chip by colloidal inkjet printing.

Provided herein are methods for inkjet printing objects, including objects which may be used as elements of microfluidic devices. The present inkjet printing methods are more amenable to mass production of microfluidic devices (critical for large-scale clinical studies) as compared to existing techniques based on injecting colloidal suspensions of silica into patterned molds. The present methods have been used to provide microfluidic devices which incorporate inkjet printed objects to facilitate the quantification of the expression and activity of exosomal matrix metalloprotease, MMP14. The present disclosure also demonstrates that exosomal MMP14 serves as a biomarker for monitoring breast cancer progression and metastasis.

Inkjet Printing Methods

In one aspect, methods for inkjet printing objects are provided. In embodiments, such a method comprises depositing a first droplet of an ink composition onto a surface of a substrate at first location. The ink composition comprises particles dispersed in a liquid phase. The method further comprises evaporating the liquid phase from the deposited droplet to form a first ring of the particles on the surface at the first location. Evaporation, which may be facilitated by using a heated substrate, induces a reorganization and self-assembly of the particles on the substrate into a ring structure of packed particles. During self-assembly, the particles generally pack closely together to minimize void space between the particles in the ring. Next, the method further comprises depositing a second droplet of the ink composition onto the surface at a second location laterally offset from the first location by a drop spacing value. (The term "laterally" and the like refers to dimensions in an xy plane defined by the substrate or an xy plane parallel to a plane defined by the substrate. Similarly, locations on the surface of the substrate may be defined by a pair of x, y coordinates.) As further described below, the drop spacing value is the distance between the centers of deposited droplets. Next, the liquid phase is evaporated to form a second ring of the particles on the surface at the second location. Generally, the drop spacing value is such that the second ring is offset from, but partially overlaps with, the first ring. These steps may be repeated as desired, including depositing an $n^{th}$ droplet and evaporating the liquid phase from the $n^{th}$ droplet to form an $n^{th}$ ring, and thus, a first set of n rings. The number of rings in a set, i.e., the integer n, is not particularly limited.

Within a set of rings, individual rings have a circular shape and are characterized by an outer diameter and an inner diameter. (As used herein, the term "circular" and the like does not mean perfectly circular, due to the inherent limitations of inkjet printing and the nature of droplet deposition/evaporation. Shapes which are elliptical or ovoid are also encompassed by the term "circular.") Individual rings are desirably continuous and unbroken, but this does not mean perfectly continuous/unbroken, in view of the inherent limitations of inkjet printing and the nature of droplet deposition/evaporation. Similarly, although individual rings define an aperture through which the underlying substrate surface is exposed, this does not mean that the substrate surface is perfectly bare as some particles from the droplet may be present.

The specific values of the outer/inner diameter of individual rings depends upon factors such as the droplet volume, particle characteristics (e.g., composition/dimensions/shape), liquid phase (e.g., composition), and substrate (e.g., composition/temperature). Various outer/inner diameters may be used, depending upon the application. However, in embodiments, the outer diameter may be in a range of from 20 μm to 40 μm. The inner diameter may be in a range of from 10 μm to 20 μm. The height of an individual ring (taken along a direction perpendicular to the substrate, i.e., in the z direction) generally corresponds to the height of a monolayer of packed particles and thus, depends upon the particle shape and dimensions. However, the height at the overlapping portion of a pair of adjacent rings may be larger due to the overlap.

The centers of individual rings are generally positioned at the x, y location on which the corresponding droplet was deposited. However, the precise centers may deviate slightly due to the inherent limitations of inkjet printing and the nature of droplet deposition/evaporation. Thus, the offset between an adjacent pair of rings is also generally given by the drop spacing value. As further described below, the drop spacing value may be selected depending upon the application. However, in embodiments, the drop spacing value is in a range of from 2 μm to 30 μm, from 2 μm to 20 μm, 2 μm to 15 μm, or 2 μm to 10 μm.

As noted above, in a set of n rings, adjacent rings are offset from one another but are partially overlapping as described above. Such a set encompasses one in which each ring of the n rings is offset from, and partially overlaps, an adjacent ring in the set. However, such a set also encompasses one in which only some of then rings are offset from, and partially overlap with, adjacent rings in the set; i.e., other rings may have no offset, and completely overlap with, adjacent rings in the set. In a set of n rings, each ring may be characterized by the same outer/inner diameter. (As used herein, the term "same" and the like does not mean perfectly the same, as there may be deviations due to the inherent limitations of inkjet printing and the nature of droplet deposition/evaporation.) Similarly, in a set of n rings, each ring may be offset from an adjacent ring by the same drop spacing value. However, sets in which some rings have different outer/inner diameters from other rings in the set and sets in which some adjacent pairs have different drop spacing values from other adjacent pairs may be formed.

An individual set of rings which has been formed as described above is shown in FIG. 1B (rightmost, labelled "1"). The number of rings in the set and the individual locations used in depositing the droplets defines an overall shape and the lateral dimensions of that shape. An individual set of rings may be referred to as a layer and an individual set/layer may also be referred to as a two-dimensional (2D) object. The overall shape of the 2D object is not particularly limited, but depends on the desired application.

Figure 1B:
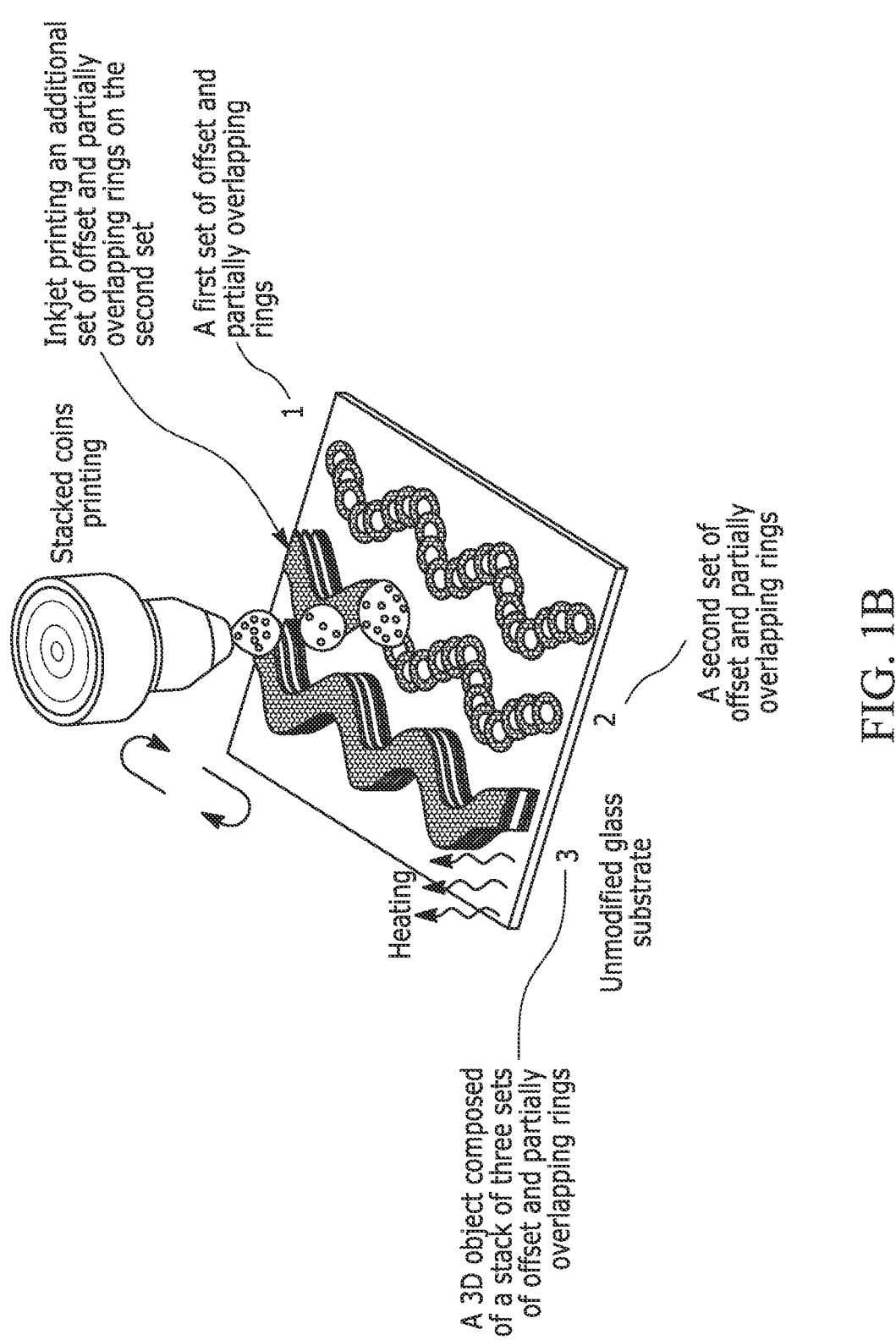

The steps above describe the formation of an individual set of rings, but the method may further comprise forming one or more additional sets of rings. As also shown in FIG. 1B (middle, labelled "2"), in forming an additional set of rings, additional droplets may be deposited using different locations as compared to the droplets deposited during formation of the first set of rings, so as to form another set of rings separated from the first. This is useful in forming an array of separated objects distributed across the surface of the substrate. However, in forming an additional set of rings, additional droplets may be deposited using the same locations as compared to the droplets deposited during formation of the first set of rings, so as to form another layer on the first set of rings. In this way, a three-dimensional (3D) object may be formed in a layer-by-layer fashion. This is also illustrated in FIG. 1B (middle, labelled "2"), showing an additional set of rings being formed on the second set of rings. FIG. 1B (leftmost, labelled "3") also shows a three-layer 3D object formed by depositing and evaporating three sets of droplets to form a stack of three sets of rings. The number of layers defines the vertical dimensions of the 3D object while the overall shape and lateral dimensions are defined by the individual sets of rings as described above.

Figure 1D:
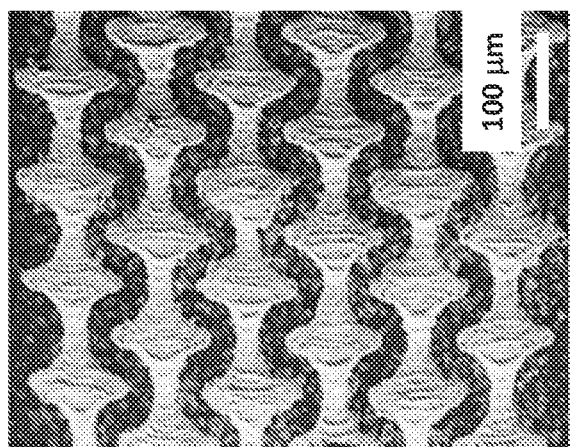
Figure 1C:
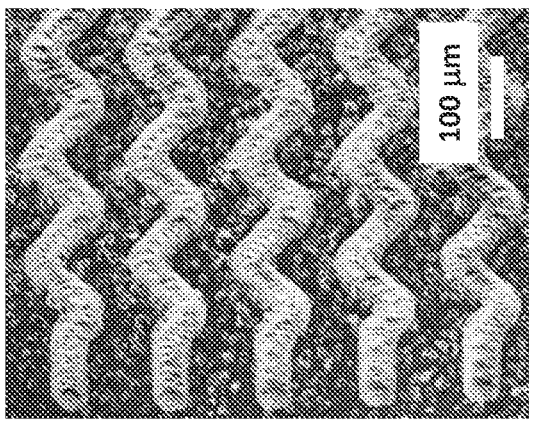

As noted above, the overall shape and dimensions of the 3D object is not particularly limited, but depends upon the application. Objects configured for use in a microfluidic device, e.g., as elements in assay chambers of such devices, may have a shape which facilitates fluid flow, fluid mixing, and/or capture of target species in fluid samples. Such shapes include a serpentine shape as shown in FIG. 1C, a zig zag shape (an array of which may form a herringbone pattern), etc. Other shapes which may be used include those shown in FIG. 1D (diamonds-on-a-string) and FIG. 1E (discrete crosses). Close-up images of an individual cross of the array of crosses show that each is composed of stacked layers of rings and rings are composed of packed spherical particles.

The 2D and 3D objects formed using the present methods are generally porous in nature, which is useful to permit fluid to flow through the objects when used as elements in microfluidic devices. The porosity may be adjusted by tuning one or more of the printing parameters (described below) as well as the particle characteristics (e.g., dimensions/shape). In addition, the particles may be functionalized after formation of the object, which may affect its porosity. For example, silica particles may be treated with an organosilane molecule, e.g., 3-mercaptopropyl trimethoxysilane (3-MPS). Among other functions, such a molecule covalently binds to surfaces of silica particles, joining adjacent particles together via silica "necks." Depending upon the amount of such functionalization, a coating may be formed over the object and may reduce its porosity.

The printing parameters used during the present methods, include the droplet spacing value, droplet volume, substrate temperature, and jetting delay. The specific values of these parameters, particularly the drop spacing value, are selected in order to achieve a set of offset but overlapping rings having a desired shape, dimensions, and resolution. The specific values which achieve this result also depend upon other factors such as the particle characteristics (e.g., composition/dimensions/shape), liquid phase (e.g., composition), and substrate (e.g., composition). However, illustrative droplet spacing values include those described above. The droplet volume may be in a range of from 1 pL to 10 pL. This includes a range from 2 pL to 8 pL, or from 4 pL to 7 pL. The substrate temperature may be in a range of from 20° C. to 50° C. This includes a range from 30° C. to 40° C. The jetting delay may be in a range of from 5 μm to 20 μm, from 5 μm to 10 μm, or from 5 μm to 10 μm.

As noted above, the present methods involve printing ink compositions which comprise particles and a liquid phase. The ink compositions are generally in the form of a colloidal suspension, i.e., the particles are homogeneously dispersed throughout the liquid phase without settling (at least on the timescale of carrying out the present methods). The particles may be composed of various materials, depending upon the application. For microfluidic applications, silica, carbon (e.g., in the form of nanotubes), and polystyrene may be used.

The particles may be characterized by their shape and various shapes may be used, e.g., spherical (which has a meaning analogous to circular as described above) and elongated (such as rods, tubes, etc.) shapes may be used. Other shapes include cubes, diamonds and prisms. Spherical shapes may be characterized by a diameter. Various diameters may be used, but for microfluidic applications, diameters in a range of from 100 nm to 5 μm are useful. This includes diameters in a range of from 500 nm to 2 μm and from 500 nm to 1 μm. Shapes such as cubes, diamonds and prisms may be characterized by a width which may have a value within the ranges described for spherical particles. Elongated shapes may be characterized by a diameter and a length. The diameters/lengths may be within the ranges described for spherical particles provided the lengths are greater than the diameters.

The particles may be present in the ink compositions at various amounts, depending upon the application. However, the amount is generally selected to facilitate printing (too much may clog the inkjet printing system) as well as to ensure ring formation (too little may inhibit formation of continuous/unbroken rings). In embodiments, the amount is in a range of from 1 weight % to 20 weight % (as compared to the total weight of the ink composition). This includes a range of from 2 weight % to 15 weight % and from 5 weight % to 10 weight %.

The liquid phase of the ink compositions may comprise a single type of liquid or multiple types of liquids. In embodiments, the liquid phase comprises, consists essentially of, or consists of water. The ink compositions may comprise additives, e.g., to facilitate printing, but in embodiments, no additives are included. For example, in embodiments, the ink composition is free of a surface tension modifier such as formamide. In fact, experiments were conducted which showed that use of such a surface tension modifier interferes with the present methods and prevents the formation of sets of offset but overlapping rings. (See Example, below.)

The ink compositions may be formed by combining the desired components at the desired amounts. However, commercially available ink compositions may also be used.

Various materials may be used for the substrate, the surface of which droplets of the ink composition are deposited using the present methods. For microfluidic device applications, silica, PMMA, and PDMS may be used. However, unlike many existing techniques for forming microfluidic devices, the substrate need not be functionalized. In fact, experiments were conducted which show that use of a functionalized surface (e.g., a glass surface functionalized with organosilane molecules to render it hydrophobic) interferes with the present methods and prevents the formation of sets of offset but overlapping rings. (See Example, below.) Thus, in embodiments, the substrate is an unmodified substrate, by which it is meant the surface is free of functional groups (other than those which may be inherent to the material from which the substrate is formed).

Various inkjet printing systems, including commercially available inkjet printing systems, may be used to carry out the present methods. Such systems generally include a print head and a holder for holding the substrate. The print head may be operably coupled to a source of the ink composition, the print head configured to jet droplets of the ink composition towards the substrate for deposition thereon. The system may further include a controller configured to control the operation of various devices of the system (e.g., the print head). The controller may include various interfaces, a computer-readable medium, a processor and a control application. Image data associated with the object to be formed may be stored in such computer-readable medium to be accessed by the processor during execution of the method. The system may be used to form 3D objects incrementally, in a layer-by-layer fashion, by depositing the ink composition in specific locations to build up successive layers, as described above, in a shape consistent with the image data.

Depending upon the application for the inkjet printed objects, the present methods may include additional steps related to further functionalizing the objects. For example, in microfluidic device applications and as further described below, it is desirable that the inkjet printed objects capture and immobilize target species in fluid samples. Thus, the inkjet printed objects may be functionalized to facilitate such capture. The type of functionalization is not particularly limited, but depends upon the composition of the particles and the target species. By way of illustration, inkjet printed silica objects may be functionalized with an organosilane molecule (e.g., 3-MPS) capable of reacting with a linking molecule (e.g., N-hydroxysuccinimide ester, GMBS) capable of reacting with an antibody (e.g., anti-CD81 monoclonal antibody) specific to a particular target species, e.g., an exosome (e.g., those present in a fluid sample from a patient).

Microfluidic Devices

As noted above, the objects inkjet printed on the substrates using the present methods may be used as elements in microfluidic devices. Such microfluidic devices are also encompassed by the present disclosure. Such microfluidic devices may comprise components such as a microfluidic channel region or layer and a pneumatic control region or layer. The microfluidic channel region/layer may comprise channels for guiding fluid flow through the microfluidic device, assay chambers in which certain tests are to be carried out, as well as valves and pumps. The pneumatic control region or layer may comprise channels for delivering air/gas for pneumatic control of the valves/pumps as well as ports for adding/removing fluid samples and fluid reagents. Such microfluidic devices generally further comprise a base on which the microfluidic channel region/layer and pneumatic control region/layer are positioned. The base provides an enclosure for features of these components, such as the assay chambers. An illustrative microfluidic device is shown in FIG. 1A, comprising a base, a microfluidic channel layer on the base, and a pneumatic control layer on the microfluidic channel layer.

The inkjet printed objects described herein may be used as elements in such microfluidic devices. For example, as described above, the present methods may be used to inkjet print arrays of 3D porous, serpentine silica stripes on a glass substrate as illustrated in FIG. 1C. This patterned substrate may be used as the base in the microfluidic device of FIG. 1A. The base and the microfluidic channel layer are aligned so that arrays are positioned within each of the assay chambers (labeled "nanopatterned microreactors" in FIG. 1A). The particular arrays of FIG. 1C provide elements which facilitate fluid flow, fluid mixing, and capture of target species in fluid samples introduced into the assay chambers. In this embodiment, the silica of the arrays is functionalized as described above to provide covalently bound antibodies (anti-CD81 monoclonal antibody) specific to exosomes excreted from cancer cells. However, other types of functionalization may be used to capture other target species. In this embodiment, the different assay chambers are in fluid communication with fluid reagents for carrying out certain assays, including an assay to quantify the proteolytic activity of a specific matrix metalloprotease, MMP14 (FIG. 1A, a1); an assay to quantify the expression of MMP14 (FIG. 1A, a2); and an assay to quantify the total exosome level (FIG. 1A, a3). Two control assays are also included (FIG. 1A, a4). The fluid reagents and conditions for each of these assays is described in the Example, below. This multiparametric microfluidic device may be referred to herein as ExoCLUE, since it achieves analysis of exosome circulation level, subtype, and enzymolytic activity. However, the type of assays carried out is not particularly limited.

Breast Cancer Biomarker

As thoroughly described in the Example, below, experiments have been conducted using microfluidic devices such as that shown in FIG. 1A. These experiments establish that tumor exosomes transport functionally active MMP14, which correlates with tumor progression and metastasis in breast cancer. Thus, such microfluidic devices may be used to test fluid samples (i.e., liquid biopsies in the form of blood, plasma, etc.) from breast cancer patients (e.g., humans) in methods of monitoring breast cancer. This is critically important to improving cancer management and developing tailored treatments for such patients.

EXAMPLE

Additional information related to this Example, including figures presenting results of experiments described in the Example and other supplementary information, may be found in U.S. Application No. 62/984,541 which is incorporated by reference in its entirety.

Introduction

Currently, while early-stage cancer generally has a favorable prognosis, most cases are diagnosed with local or distant metastases that lead to ~90% of deaths from cancer. Poor survival of advanced cancer has been related to the lack of effective therapies and emergent drug resistance, attributed to molecular heterogeneity of tumors and divergent clonal evolution during disease development and treatment. Such diverse tumor dynamics pose a major challenge to clinical management of advanced cancer, which requires real-time assessment of disease states to inform decision making and to optimize treatment. While widely used in the clinic, radiographic imaging often fails to detect changes in tumor burden. Genomics centered on gene alterations faces challenges in capturing instant status of malignancy, such as invasive/metastatic phenotypes. Moreover, longitudinal surveillance of tumor evolution is crucial to clinical implementation of precision medicine; however, conventional tissue biopsy is invasive, constrained to a localized snapshot of the tumor, and often unrepeatable. Thus, novel tools that complement current methods for accurate tracking of tumor dynamics are urgently needed to improve disease stratification, prognostic prediction, and early detection of metastasis for optimal treatment.

Liquid biopsy offers an attractive alternative for cancer diagnosis and treatment. Rapidly emerging as a new paradigm of liquid biopsy, extracellular vesicles (EVs), including exosomes, promise to complement circulating tumor cells and DNA to derive a global molecular landscape of solid tumors. This is owing to the distinct properties of these nanovesicles which are i) enriched with selectively sorted original cell contents, ii) actively released from live cells instead of shed from apoptotic or damaged cells, and iii) relatively stable in bodily fluids. EVs have been extensively identified as important cell communication mediators and implicated in tumor development and metastasis via various processes, such as epithelial-mesenchymal transition (EMT), extracellular matrix (ECM) remodeling, and formation of pre-metastatic niches. Relevant to this Example, EVs derived from tumors and stromal cells in tumor microenvironments were found to carry matrix metalloproteinases (MMPs), a key regulator of ECM. In particular, tumor-derived EVs, including exosomes, were shown to carry functionally active MMP14 that not only degrades type 1 collagen and gelatin, but also promotes the expression and activation of other MMPs to enhance the remodeling of ECM. Despite these provocative findings, very limited progress has been reported in exploring the clinical value of MMP-mediated functions of EVs in tumor progression and metastasis.

Clinical study of EVs is largely hindered by a number of key practical challenges, including the lack of standardized methods for efficient and unbiased EV isolation, general unavailability of ultrasensitive and robust biosensing systems for rapid analysis of large clinical cohorts, large sample consumption and assay cost, and poorly defined physical and biochemical markers to distinct tumor-specific EVs from a vast background of host cell EVs. Microfluidics have been extensively applied to address these challenges owing to its inherent advantages in sample consumption and analytical performance. A microfluidic colloidal self-assembly (μCSA) strategy was recently developed for 3D nanoengineering of microfluidic biosensors, which immensely improves the sensitivity for small EV (sEV) detection via overcoming the fundamental limits in mass transfer, surface reaction, and boundary effects simultaneously. Compared to the existing microfluidic technologies, including the prototype nanochips, the present Example provides distinct innovations in device engineering and EV marker studies, focusing on improving the translatability for clinical applications.

First, distinct from the μCSA-based strategy, a generalized, high-resolution colloidal inkjet printing method was developed, which is much more amenable to mass production of 3D nanoengineered chips for large-scale clinical studies. Compared to the previous inkjet printing techniques, the method affords much improved printing resolution (down to 20 μm) and enables rapid printing of complex, large-scale 3D colloidal nanostructures without the need for surface pretreatment. Second, despite well-demonstrated applications to molecular analysis of EVs, microfluidic technology has not been explored to assess the functional activities of EVs as cancer signatures. A nano-engineered lab-on-a-chip system was devised for multiparametric analysis of EV circulation level, subtype, and enzymolytic activity (EV-CLUE) with ultrahigh sensitivity and minuscule sample input. Such analytical capabilities enabled longitudinal monitoring of in vivo tumor growth in single mice, which could open new opportunities to advance animal studies of cancer. Third, while EV-mediated transport of MMP14 has been implicated in tumor invasion and metastasis, the clinical value of EV MMP14 marker remains largely unexplored. In this study, the MMP14 expression and activity phenotypes of EVs for detecting tumor invasion and metastasis were investigated, using various cell lines, mouse models, and clinical plasma specimen. It was shown that the nanochip-based assay could vastly improve the diagnostic performance of EV MMP markers over the standard assays. Thus, the present technology provides a new liquid biopsy tool for longitudinal surveillance of tumor evolution in patients to improve cancer management and precision medicine.

Methods

This Example sought to investigate EV-transported MMP-14 as a potential biomarker for monitoring tumor progression and metastasis using a 3D nanopatterned Exo-CLUE lab-on-a-chip system. A high-resolution colloidal inkjet printing technique was developed for confer robust and scalable 3D nanopatterning to augment the potential translatability of this technology. The ExoCLUE chip was designed to integrate the EV ELISA and MMP14 activity assays in parallel for multiparametric analysis of the total concentration and MMP14 expression and activity of EVs in blood plasma. The nanochip-based assays were assessed and optimized to afford the balanced sensitivity and specificity for measuring in vitro cell invasiveness, using various standard cancer cell lines and the isogenic breast and pancreatic cancer cell clones created by CRISPR/Cas9 editing. With the experimental and spontaneous mouse models of breast cancer metastasis, the ExoCLUE chip was further optimized and validated for longitudinal monitoring of in vivo tumor growth and metastasis in single mice. Lastly, the feasibility of our technology and the sEV MMP14 markers for clinical detection and staging of breast cancer were assessed using the plasma samples from two independent training (n=30) and validation cohorts (n=70) composed of age-matched cancer-free controls and DCIS, non-metastatic IDC, and locally metastatic breast cancer patients. The samples for each patient group were randomly pulled out to represent diverse histological and molecular subtypes, including TNBC. A machine learning based diagnostic was combined with the chip-based integrative functional EV analysis to enhance the clinical sensitivity and specificity for patient classification. Furthermore, extensive comparative and correlation studies with standard analytical methods were performed to validate the ExoCLUE measurements. Three technical replicates were conducted for all measurements.

Reagents and Materials. 10% (w/w) monodispersed silica colloids were purchased from Bangs Laboratories Inc. (3-Mercaptopropyl) trimethoxysilane (3-MPS), 4-Maleimidobutyric acid N-hydroxysuccinimide ester (GMBS) were purchased from Sigma-Aldrich. Formamide was obtained from Fisher Scientific. The ELISA kits for MMP14, MMP15, and MMP16 were ordered from R&D Systems and contained capture antibody, standard protein, and detection antibody. Streptavidin conjugated β-Galactosidase (SβG), Fluorescein-di-β-D-galactopyranoside (FDG), and Vybrant™ CM-Dil cell staining solution were purchased from Life Technologies. The FRET peptide substrate of MMP14 (SensoLyte 520) was ordered from AnaSpec Inc. The detailed information of antibodies used in the studies was listed in the supplementary information of U.S. Application No. 62/984,541, which is incorporated by reference in its entirety. 1×PBS solution and SuperBlock buffer were from Mediatech, Inc and ThermoFisher Scientific, respectively. All other solutions were prepared with deionized water (18.2 MV-cm, Millipore). SβG and FDG were dissolved in PBS working solution (PBSW) at pH 7.4, which contained 0.5 mM DL-dithiothreitol (Sigma-Aldrich), 2 mM MgCl$_2$ (Fluka Analytical), and 0.5% bovine serum albumin (BSA, Sigma-Aldrich).

Colloidal inkjet printing. A piezoelectric drop-on-demand inkjet printer DMP-2850 (Fujifilm Dimatix, Inc., CA) was used for colloidal printing with a cartridge (Model No. DMC-11610) that supports 10 pL droplets. The printer head consisted of 16 nozzles in a row, and the operation of each nozzle could be controlled individually. The center-to-center drop spacing was adjustable in one-micron increments within a 5 to 254 μm range. The patterns were designed with AutoCAD and then converted into the bitmap images for printer input. Prior to printing, the glass substrate was cleaned thoroughly with DI water under sonication. For "stacked coins" printing mode, only one nozzle was used, and the temperature of the substrate was set to 50° C. to ensure that the evaporation time of a single drop was less than the drop jetting period. The drop size was adjusted by controlling the voltage of cartridge, which was optimized to be 15 kV. For multi-layer printing, the inter-layer delay was 60 s.

Fabrication of EV-CLUE chip. Two-layer PDMS chips were fabricated by multi-layer soft lithography according to an established protocol. Briefly, silicon wafers were cleaned with piranha solution and spin-coated with 30 μm thick SU-8 2025 photoresist (MicroChem). The SU-8 microstructures were fabricated onto the wafers from the photomasks, following the protocols recommended by the manufacturer. Prior to use, the SU-8 molds were treated with trichloro(1H, 1H,2H,2H-perfluorooctyl)silane (Sigma-Aldrich) under vacuum for 8 h. To fabricate the pneumatic layer, 30 g mixture of PDMS base and curing agent at a 7:1 ratio was poured on the mold and cured in the oven at 70° C. for 2 h. The PDMS pieces were peeled off from the mold, cut, and punched to make pneumatic connection holes. Meanwhile, the fluidic layer was prepared by spin-coating the mold with a 5 g mixture of PDMS base and curing agent at a ratio of 15:1 at 1000 rpm for 45 s, followed by curing on a 70° C. hotplate for 30 min. The pneumatic layer was then manually aligned with the bottom fluidic layer under a stereomicroscope and permanently bonded by baking in the 70° C. oven overnight. The printed 3D nanopatterns were treated with 5% 3-MPS in ethanol for 1 h, followed by heating at 80° C. for half an hour to stabilize the nanostructures. The coated nanopatterns were then treated with 0.28 mg/mL GMBS for 0.5 h, which was used as a linker to immobilize the antibody. Using a patterning chip, the nanopatterns were washed with PBS, and then 0.1 mg/mL anti-CD81 capture antibody was flowed through and incubated for 1 h at room temperature. After washing with PBS, the patterning chip was removed and the modified nanopatterns were then aligned and assembled with a flow-channel chip to construct the complete microfluidic system. Finally, the channel surface was blocked with 5% BSA for 1 h and stored at 4° C. before use. For SEM characterization, the nanopatterns were coated with ~5 nm gold using a high-resolution ion bean coater and then imaged with an FEI Versa 3D Dual Beam scanning electron microscope.

sEV ELISA and activity assays on chip. The lyophilized standard EVs of COLO-1, MCF7, and MDA-MB-436 cell lines were purchased from HansaBioMed, Ltd (Tallinn, Estonia) and reconstituted in water prior to use. 5-10 µL samples (purified EVs or 5× diluted plasma) were added into the inlet of each unit on the EV-CLUE chip and pneumatically pumped through at an average flow rate of ~0.1 µL/min in a "stop-flow" manner. After immuno-capture of sEVs, unbounded species were washed with 10 µL PBS. For ELISA detection, specific biotinylated detection antibodies (a cocktail of CD9 and CD63, or MMP14, 20 µg/mL) were injected and reacted for 1 h. Excess antibodies were washed by PBS, and SβG prepared in PBSW buffer (20 ng/mL) was introduced as the reporter enzyme. After another 10 min washing with 10 µL SuperBlock buffer, FDG in PBSW (500 µM) was injected into the chamber and reacted in the dark for 0.5 h before imaging readout. For the parallel enzymatic activity assays, PBS was injected instead of the detection antibody and SβG was used for the sEV ELISA. The FRET peptide substrate of MMP14 was then injected into the activity assay chambers and reacted for 1 h before imaging. Fluorescence images were taken using a Zeiss Axiovert A1 inverted fluorescence microscope equipped with a LED excitation light source (Thorlabs, Newton, NJ). Digital images were processed using ImageJ (NIH, http://rsbweb.nih.gov/ij/) to quantify the fluorescence intensity.

Characterization of surface-captured sEVs followed established protocols. (Zhang, P. et al. *Nat Biomed Eng* 3, 438-451 (2019).) Briefly, for SEM, sEVs were fixed with 2.5% glutaraldehyde in PBS for 30 minutes and 1% osmium tetroxide for 15 minutes, and then rinsed with water for 10 minutes. The samples were dehydrated in ethanol with a gradually increasing fraction (30%, 50%, 70%, 95% and 100%) for 2×10 min each, coated with a gold thin film, and then examined with an FEI Versa 3D Dual Beam SEM. Confocal imaging was done with an Olympus 31 spinning disk confocal epifluorescence TIRF inverted microscope. Image stacks were taken in a 1 µm interval along the z-axis, which ranged from the bottom of the nanostructures to the top of flow channel. The obtained image stacks were fitted into 3D view photography using SlideBook version 5.5.

Cell lines and culture conditions. Human cancer cell line MDA-MB-231 and MIAPaCa2 were purchased from American Type Culture Collection. To generate HuR knock-out sublines, MDA-MB-231 and MIAPaCa2 cells were infected with LentiCRISPRv2 lentiviral vector (Addgene, Cambridge, MA) to stably express control sgRNA or HuR sgRNAs. The cells were then under puromycin selection for two weeks and single clones were generated. These cell lines were cultured in DMEM (Mediatech, Manassas, VA) supplemented with 10% fetal bovine serum (FBS; Sigma-Aldrich, St. Louis, MO), 1% Glutamine (Mediatech), and 1% antibiotics (Mediatech) in a 5% $CO_2$ humidified incubator at 37° C. For sEV studies, cells were grown in culture media that contained 10% FBS depleted of EVs (Gibco, Grand Island, N.Y.). At confluency, cell medium was collected and immediately used for sEV isolation.

Ultracentrifugation isolation of EVs. The supernatant of cell culture media was centrifuged at 4° C. at 2,000×g for 10 min to remove large cell debris, 10,000×g for 45 minutes to remove large vesicles, and at 100,000×g for 2 h to pellet EVs. The supernatant was carefully removed and EV pellets were then resuspended in 10 mL of PBS for washing and collected again with UC at 4° C. for 60 min at 110,000×g in Beckman Coulter Quik-Seal Centrifuge Tubes. After aspiration of the supernatant, EV pellet was resuspended in 100 µL PBS. The aliquots of isolated EVs were stored at −80° C.

Western Blot analysis. Western blotting was performed using 4-12% precast polyacrylamide slab mini-gels (Tris-glycine pH 8.3) with Blot Module (Bio-Rad), following the standard protocol. 30 µg cell lysate or ~$10^{10}$ EVs were pretreated with RIPA lysis buffer with protease inhibitors on ice for 45 min and heated at 72° C. for 10 min after adding equal volume of 2× loading buffer. The electrophoresis was carried out at 125 V for 2 hrs, and then gels were electro-transferred to the cellulose membranes (0.2 µm) at 25 V for 2.5 hrs. The NC membrane was first blocked with Odyssey® Blocking Buffer (PBS), then incubated overnight at 4° C. in primary antibodies: rabbit anti-MMP14 (1:500), mouse anti-HuR (1:500), mouse anti-α-tubulin (1:1000), and mouse anti-CD81 (1:1000). The membranes were washed 3 times for 10 min each (1×PBS, 0.5% Tween 20, pH 7.4) and then incubated with anti-mouse or anti-rabbit IRDye 680 (1:7500) or 800(1:15000) from LI-COR (Lincoln, NE) for 60 minutes at room temperature. After that, the washing step was repeated three times. Imaging was performed using an Odyssey Fc Imaging System (LI-COR Biosciences).

Cell invasion assay. To analyze cell invasion, Corning BioCoat Matrigel Invasion Chambers (Bedford, MA) were used. 1×$10^5$ cells in 0.5 mL of serum free medium were seeded in Matrigel-coated upper chambers and incubated for 22 h at 37° C., 5% $CO_2$ atmosphere. Cells were fixed with 95% methanol and stained with 0.1% crystal violet. Non-invading cells were removed from the upper surface of the membrane by cotton swabs. Cells that invaded were visualized and photographed with EVOS FL cell imaging systems (Life Technologies, Bothell, WA) under 4× and 20× magnification.

Animal experiments. In the experimental metastasis model, 1×$10^6$ 2LMP cells stably expressing luciferase were injected into tail veins of 4-week-old female nude mice. Bioluminescence imaging was taken weekly to monitor tumor burden at lung. Specifically, mice were interperitoneally injected with 150 mg/kg D-luciferin dissolved in PBS, anesthetized, and imaged in MS FX PRO small animal imaging systems. At each time point specified in the main text, ~50 µL, blood was collected from tail veins of mice in the EDTA-coated tubes (Microvette® 100 K3E, Sarstedt AG Co., Nümbrecht, Germany) to prepare plasma samples for microfluidic sEV profiling. In the spontaneous metastasis model, 0.5×$10^6$ 4T1 cells stably expressing luciferase were injected into #4 mammary fat pad of 4-week-old female BALB/c mice. Primary tumor sizes were measured using a caliper twice a week. Tumor volume was calculated using the formula: (length×$width^2$)/2. Bioluminescence imaging was taken weekly to monitor the primary tumor and the metastasis burden at lung. ~50 µL blood was collected from tail veins of mice weekly with the EDTA-coated tubes (Microvette® 100 K3E), and plasma was immediately prepared for on-chip sEV analysis.

Patient specimen and clinical EV analysis. De-identified plasma samples from breast cancer patients and cancer-free individuals with accompanying clinical information (see the supplementary information of U.S. Application No. 62/984, 541, which is incorporated by reference in its entirety) were obtained from the KU Cancer Center's Biospecimen Repository Core Facility (BRCF). Blood specimens, i.e., plasma samples, were collected from women enrolled under the repository's Institutional Review Board (IRB)— approved protocol (HSC #5929) and following U.S. Common Rule. Once the patient provided written, informed consent in accordance with the BRCF's IRB protocol, blood was collected by BRCF staff and processed for long-term storage at −80° C. In this study, the vast majority of patients had ductal carcinomas because of its dominant prevalence in breast cancer (>80%) compared to lobular carcinomas which account for only ~10-15% of cases. The required sample size for evaluating diagnostic accuracy was estimated via comparing the area under a ROC curve (AUC) with a null hypothesis value of 0.5. For conventional characterization of the samples, EVs were purified by UC and then characterized by NTA sizing, Bradford assay, and Western blot, following established protocols. (He, M. et al., *Lab Chip* 14, 3773-3780 (2014).) For microfluidic analysis, 6-μL plasma was diluted with PBS by 5 times to prevent channel clogging and was used without any further pretreatment. SEV assay and data acquisition followed the same processes as for EV standards. For EV analysis with the standard ELISA method, an ExoTEST™ Ready-to-Use Kit purchased from HansaBioMed, Ltd (Tallinn, Estonia) was used, following the established protocol. (Zhang, P. et al. *Nat Biomed Eng* 3, 438-451 (2019).) Briefly, 10 μL plasma samples were 10-fold diluted to 100 μL and then added into each well of a 96-well plate. The microplate was incubated on a microplate shaker at room temperature for 30 min and then put in a 4° C. fridge for overnight incubation. The plate was washed with 200 μL of washing buffer per well 3 times and incubated with 100 μL of the biotinylated anti-MMP14 detection antibody (2 μg/mL) for 30 min at room temperature and 2 h at 4° C. The plate was washed 3 times, incubated with 100 μL of 1:5000 diluted HRP-streptavidin conjugate (15 min at room temperature and 1 h at 4° C.), washed 3 times, and then incubated with 100 μL of chromogenic substrate solution in the dark for 10 min at room temperature. After adding 100 μL of stop solution, absorbance at 450 nm was measured on a CYTATION 5 imaging reader (BioTek) and subtracted by the background measured with PBS.

Histological analysis of patient-matched tissues. H&E and IHC staining were performed in the Histology Laboratory at the KU Cancer Center according to the following procedure. Four micron paraffin sections were mounted on Fisherbrand Superfrost slides and baked for 60 min at 60° C. then deparaffinized. Epitope retrieval was performed using a Biocare Decloaking Chamber (pressure cooker) under pressure for 5 min, using pH 6.0 Citrate buffer followed by a 10 min cool down period. Endogenous peroxidase was blocked with 3% $H_2O_2$ for 10 min followed by incubation with a specific primary antibody for 30 min: 1:400 dilution of monoclonal MMP14 (Clone #5H2) (R&D, MAB918). This was followed by Envision+ anti-mouse secondary (Dako) for 30 min and DAB+ chromogen (Dako) for 5 min. IHC staining was performed using the IntelliPATH FLX Automated Stainer at room temperature. A light hematoxylin counterstain was performed, following which the slides were dehydrated, cleared, and mounted using permanent mounting media.

Statistical analysis. Mean, standard deviation, standard error of mean, and LOD were calculated with standard formulas. To quantify the correlation between different variables, Deming linear fitting was performed at the 95% confidence level to determine the Pearson correlation coefficient. To determine if parametric or non-parametric tests would be used for statistical comparisons, a normality test was conducted and it was found that the assumption of normality could not be rejected for the cell line and mouse model data, but was rejected for the data of human subjects, at the significance level of P<0.05. Hence, for cell line experiments, two-tailed Student's t-test was performed for two-group comparison and one-way ANOVA with post-hoc Tukey's pairwise multiple comparisons test for multi-group comparison. In the studies of mouse models, statistical comparison among different time points was conducted with one-way repeated measures ANOVA with post-hoc Tukey's test. Tumor growth in the mouse groups with or without lung metastasis developed was assessed by two-way ANOVA followed by the Tukey's test. In the analyses of human specimen, group difference was assessed using non-parametric, two-tailed Mann-Whitney U-test for two groups or Kruskal-Wallis one-way ANOVA with post hoc Dunn's pairwise multiple comparisons test for multiple groups. An LDA-based ROC analysis was adopted to evaluate the diagnostic metrics of biomarkers. The training set data was first processed by LDA to classify the subjects into the control and cancer groups, and the resultant discriminant function model was used for binary classification of the validation cohort without known a priori disease state. The predicted probabilities yielded for both training and validation cohorts were used to conduct ROC curves. Optimal cutoff points were selected using the maximum Youden's index to determine the sensitivity, specificity, and accuracy of disease diagnosis. For multi-group classification, quadratic discriminant analysis was conducted as the equality test of within-group covariance matrices failed. The training cohort was first analyzed to generate the discriminant function model which was used to classify the patients in the validation cohort. 95% CIs for AUC were determined using the DeLong method, and exact CIs for sensitivity, specificity, and accuracy were calculated based on the binomial distribution. 95% confidence level was used in all statistical analyses, which were performed using Excel 2018, OriginPro 2019, and GraphPad Prism 8.

Results

3D Nanopatterning of EV-CLUE Chips by Colloidal Inkjet Printing

FIGS. 1A-1E illustrate the design and working principle of the EV-CLUE chip, as well as its fabrication based on a robust 3D colloidal inkjet printing method. As seen in FIG. 1A, the EV-CLUE chip is a polydimethylsiloxane (PDMS)/ glass hybrid device composed of a pneumatic control circuit and an array of eight parallel microchambers patterned with 3D nanostructured microelements to enhance immunological analysis of circulating sEVs. These microchambers were flanked by two normally closed valves to form the enclosed microreactors for enzymatic detection. Three sEV assays were implemented on the integrated microchip in parallel. A fluorogenic activity assay was developed that immunocaptured sEVs and specifically measured the proteolytic activity of sEV-carried MMP14 using a fluorescence resonance energy transfer (FRET) peptide probe (FIG. 1A, a1). This peptide substrate for MMP14 was labeled with a fluorophore and a quencher which could be enzymatically cleaved by MMP14 to generate fluorescence signal. Two exo-ELISA assays were also established on chip to quantify the MMP14 protein present on sEVs (FIG. 1A, a2) and the total sEV abundance by probing CD63 and CD9 (FIG. 1A, a3), respectively. The eight-channel design permitted simultaneous analysis of two samples, along with two negative control assays using the phosphate-buffered saline (PBS) blank to determine the backgrounds for the activity and expression assays, respectively. Briefly, the fabrication process involved first depositing the 3D nanostructured micropatterns on a glass slide, which were then strengthened by 5%

3-MPS silane treatment and thermal hardened, and finally sealed with a pre-fabricated PDMS assay chip (see the Methods for details).

In contrast to previous μcSA strategies, here a general inkjet printing method was developed that presents a key engineering advance to address the challenges in robust, scalable manufacturing of 3D nanopatterned microfluidic biochips. Colloidal inkjet printing is an attractive patterning technique for fabrication of nanomaterials-based devices for many applications. Current colloidal printing techniques control the geometry and quality of patterns by exploiting surface modifications to delicately adjust the interactions between surface wetting and evaporation-driven CSA. This strategy limits the ability to print complex colloidal structures due to the challenges in controlling interfacial interactions during drying. Indeed, conventional printing protocols have been optimized, but failed to print an array of sinusoidal stripes as described in U.S. Application No. 62/984,541, which is incorporated by reference in its entirety. Compared to hydrophobic glass surfaces treated by silanization, a hydrophilic surface is more compatible with printing of continuous structures. However, the droplets printed on a hydrophilic substrate can easily merge and spread, owing to the low surface tension, which leads to poor printing resolution and severely distorted geometries. Evaporation of a drop of colloidal suspension on a hydrophilic surface produces a donut pattern of packed colloids due to the "coffee ring" effect. While adding formamide in the solvent can reduce coffee-ring effect during evaporation to produce more uniform assembly of colloids, the surface tension will be further decreased, resulting in even worse printing resolution and pattern quality.

Distinct from the conventional strategies, here a "stacked coins" printing approach was established that exploits the coffee ring phenomenon to print continuous 3D colloidal patterns on an unmodified glass surface (FIG. 1B). The droplet volume, substrate temperature, and jetting delay period were adjusted such that colloidal ring patterns could be deposited individually and overlapped with each other like offset stacked coins. Multi-cycle, repeated printing stacked the layers of packed colloids to fill the void areas among the ring patterns, creating a 3D structure of designed geometries. In this printing process, drop spacing is a crucial factor that affects the final morphology of the printed structures. Therefore, a range of 5-20 μm was investigated for printing with a 5% (w/w) solution of 1 silica colloids, and the drop spacing of 10 μm appeared to yield the best printing quality. Using the optimized protocol, a 5-cycle printing of 1 μm silica colloids was demonstrated, to print a centimeter-scale graphic design on a plain glass slide (not shown). The printed pattern exhibited angle-dependent iridescent structural colors owing to Bragg scattering of light by the ordered nanostructure of self-organized colloids. Either uniform structural colors or smooth spectra were observed across the entire pattern, indicating the high quality of the printed nanomaterial structures.

Figure 1E:
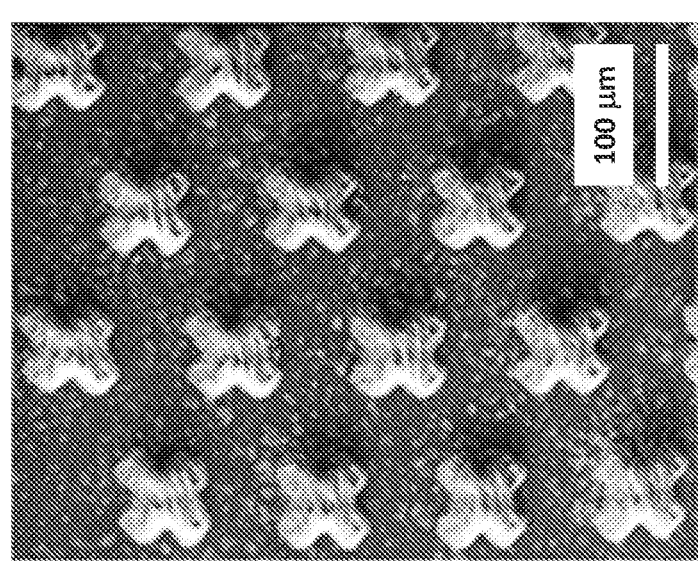

To further assess the stacked-coins printing method, 15-cycle printing was tested of various micropatterns of 1 μm silica colloids (5% w/w), such as the arrays of sinusoidal strips, diamonds, and X shapes. Scanning electron microscopy (SEM) and optical profilometry were used to determine the morphology, height, and surface roughness of the printed micropatterns. The SEM images and corresponding surface profiling plots confirmed that this method was able to produce 3D self-assembled colloidal patterns of designed geometries (FIGS. 1C-1E). The inkjet printing resulted in greater structural roughness than the microchannel molding-based μCSA fabrication. Surface profiling by 3D profilometry determined the heights of these patterns to be varying from ~14 to 22 μm. Such topological roughness is expected for the inkjet printing and can be further optimized by tuning the printing parameters, such as drop spacing and sizes. Nonetheless, rough morphology is favorable to this particular application, because it confers greatly increased surface area to enhance EV immunocapture. By testing with the X shapes consisting of 40-μm wide bars, the geometric resolution of this printing method was estimated to be ~20 High-magnification SEM verified the highly nanoporous structure of the printed micropatterns and visualized the silica nanoparticles being glued together by the 3-MPS treatment, which strengthens the mechanical stability of printed silica micropatterns. Moreover, compared to the microchannel-confined CSA method, open surface printing greatly improves the scalability and the success rate of device fabrication, as it negates the requirement for manually removing the patterning chip which can cause mechanical damage of the deposited micropatterns. It is worth noting that this printing method does not require sophisticated control of the balance among substrate chemistry, ink composition, and printing conditions as is needed by the conventional printing approaches. Thus, this method not only simplifies device manufacturing, but also expands the potential applications owing to the ease to implement variable surface chemistries, which is pivotal to biosensing. Overall, these results demonstrate that the present inkjet printing technology provides a general approach capable of high-resolution printing of large-area, complex patterns on hydrophilic surfaces without any chemical pre-treatment.

Integrative Molecular and Functional Phenotyping of sEVs by EV-CLUE Chip

The EV-CLUE chip was first studied for sEV immunocapture using a colon cancer COLO-1 cell-derived EV standard which has been well characterized. (Zhang, P. et al., *Lab Chip* 16, 3033-3042 (2016).) Sinusoidal patterns were printed inside the assay microchambers by the 15-cycle printing protocol (FIG. 1B). Fluorescently stained COLO-1 EVs were spiked at $10^6$ μL$^{-1}$ in 10-fold diluted healthy human plasma and injected into the chip coated with the anti-CD81 monoclonal antibody (mAb). The confocal fluorescence microscopy images acquired at various depths showed that COLO-1 sEVs were captured on both external and interior surfaces of the printed 3D nanoporous micropatterns with a decreasing density gradient inward, indicating the flow penetration through the pores of printed nanoparticle assemblies. SEM imaging visualized high-density capture of sEVs on the mAb-modified silica nanoparticles and the typical spherical and cup-shaped morphologies of captured sEVs. The size range of chip-captured EVs was estimated to be 40 to 160 nm from the SEM images, smaller than that of the original UC-purified EVs (~50 to 350 nm) measured by nanoparticle tracking analysis (NTA).

Figures 2A, 2B:
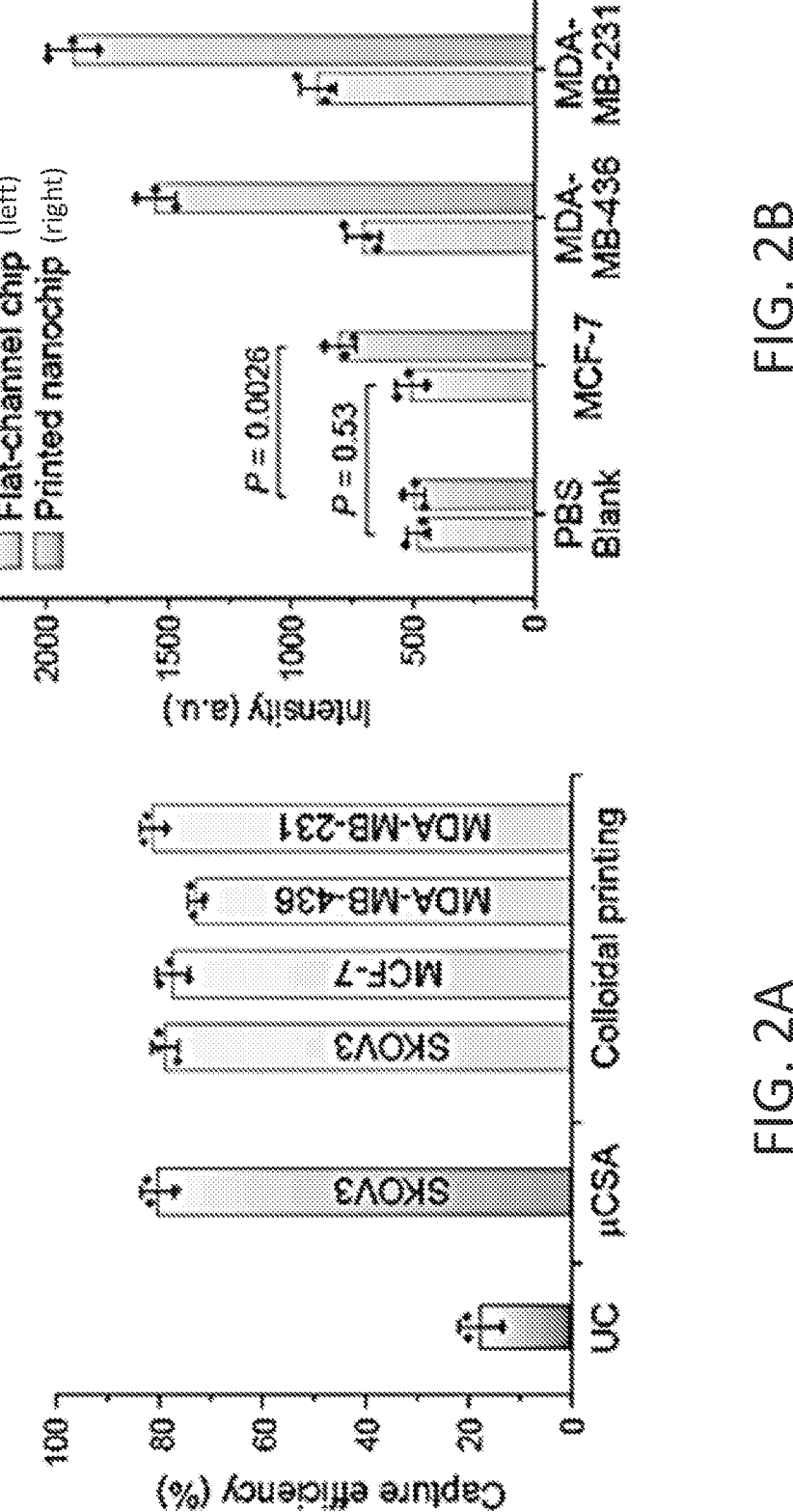
FIGS. 2A-2D demonstrate the characterization of the EV-CLUE chip for immuno-isolation and integrative molecular and activity phenotyping of sEVs.

The capture efficiency of EV-CLUE nanochips was evaluated in comparison with the gold standard ultracentrifugation (UC) and the μCSA-engineered chips. EVs of various cancer cell lines were purified from the conditioned culture media and characterized by NTA to prepare the standards of known quantities for the technology development. Here the anti-CD81 mAb-coated nanochips were assessed for sEV capture, following an established depletion method. (Zhang, P. et al. *Nat Biomed Eng* 3, 438-451 (2019).) Using the cell-derived EVs that were stained with a non-specific membrane-tracking fluorescent dye and spiked in healthy plasma at $10^6$ μL$^{-1}$, the capture efficiency observed for four cell lines of ovarian and breast cancers were 78.2±2.6% for SKOV3, 77.4±3.1% for MCF-7, 72.9±1.5% for MDA-MB-436, and 81.3±3.4% for MDA-MB-231 (FIG. 2A). Such relatively consistent capture efficiency across various cell lines and cancer types permitted downstream quantitative detection of captured sEVs and their molecular constituents. The capture performance of the printed chips was found to be comparable to that of the μCSA-engineered devices (80.3±3.2% for SKOV3) and much higher than that of standard UC isolation (17.9±3.9%). In contrast, sEV isolation using the control chips coated with BSA resulted in very low non-specific binding (<6.7%), indicating the effectiveness of the assay protocol to suppress the matrix effects on the nano-patterned chip. These comparative studies show that the inkjet printing method provides an effective means for nanoengineering of microchips to improve sEV immuno-isolation and downstream analysis, as further demonstrated below.

Based on the nanochip immunocapture, an attempt was made to develop the sandwich MMP ELISA and proteolytic activity assays for molecular and functional phenotyping of tumor-derived sEVs. Here MMP14 was targeted, as it has been credited as a central regulator of cell invasion via degrading major components of ECM (e.g., fibrillar collagens, fibronectin, and vitronectin) and processing a host of intra- and extracellular proteins (e.g., soluble pro-MMPs, cytokines, and growth factors) to promote matrix remodeling and invasive behavior of tumor cells. As a test case, three breast cancer cell lines were used, including weakly invasive MCF7 cells as the control and two triple negative breast cancer (TNBC) cell lines, MDA-MB-436 and MDA-MB-231, with increasing metastatic capability. Among three tetraspanins commonly used for sEV capture, CD81 was found to yield the highest detection sensitivity for these cell lines. Thus, the assays were configured to capture overall sEVs by anti-CD81 mAb and measure the expression and activity of sEV-bound MMP14 with specific mAb and peptide probes, respectively. It was demonstrated that this nanochip-based immunoassay permits sensitive detection of the low-abundance MMP14+ subpopulation in MCF7-derived EVs, which was otherwise undetectable to the same assay conducted on a conventional flat-channel chip (FIG. 2B). Higher MMP14 expression was detected in EVs from metastatic MDA-MB-436 and MDA-MB-231, compared to that of MCF7 cells. It was also demonstrated that the printing-based 3D nanostructuring of microfluidic chips immensely improved detection sensitivity of sEV ELISA. The chip detection of MMP14 was further verified by standard Western blot and microplate enzymatic activity assays.

The sandwich activity assay was then developed by combining sEV immunocapture with the detection of enzymatic activity of MMP14 using a FRET peptide substrate (FIG. 1A). Using a standard microplate assay kit, a commercially available fluorogenic probe was selected and verified for its specificity to MMP14 protein against three soluble and membrane MMPs commonly associated with breast cancer: MMP9, MMP15, and MMP16. Chemical activation of recombinant pro-MMP14 protein by 4-aminophenylmercuric acetate (APMA) was required to gain enzymatic activity. In contrast, similar MMP14 activity was detected for EVs of various breast cancer cells with and without chemical activation, indicating sEV MMP14 being prevalently activated. The MMP14 activity assay was conducted without chemical treatment to measure the native activity of circulating sEVs. Lastly, the enzymatic reaction time for the on-chip fluorogenic activity assay was optimized to afford a maximal signal/noise ratio.

Figures 2C, 2D:
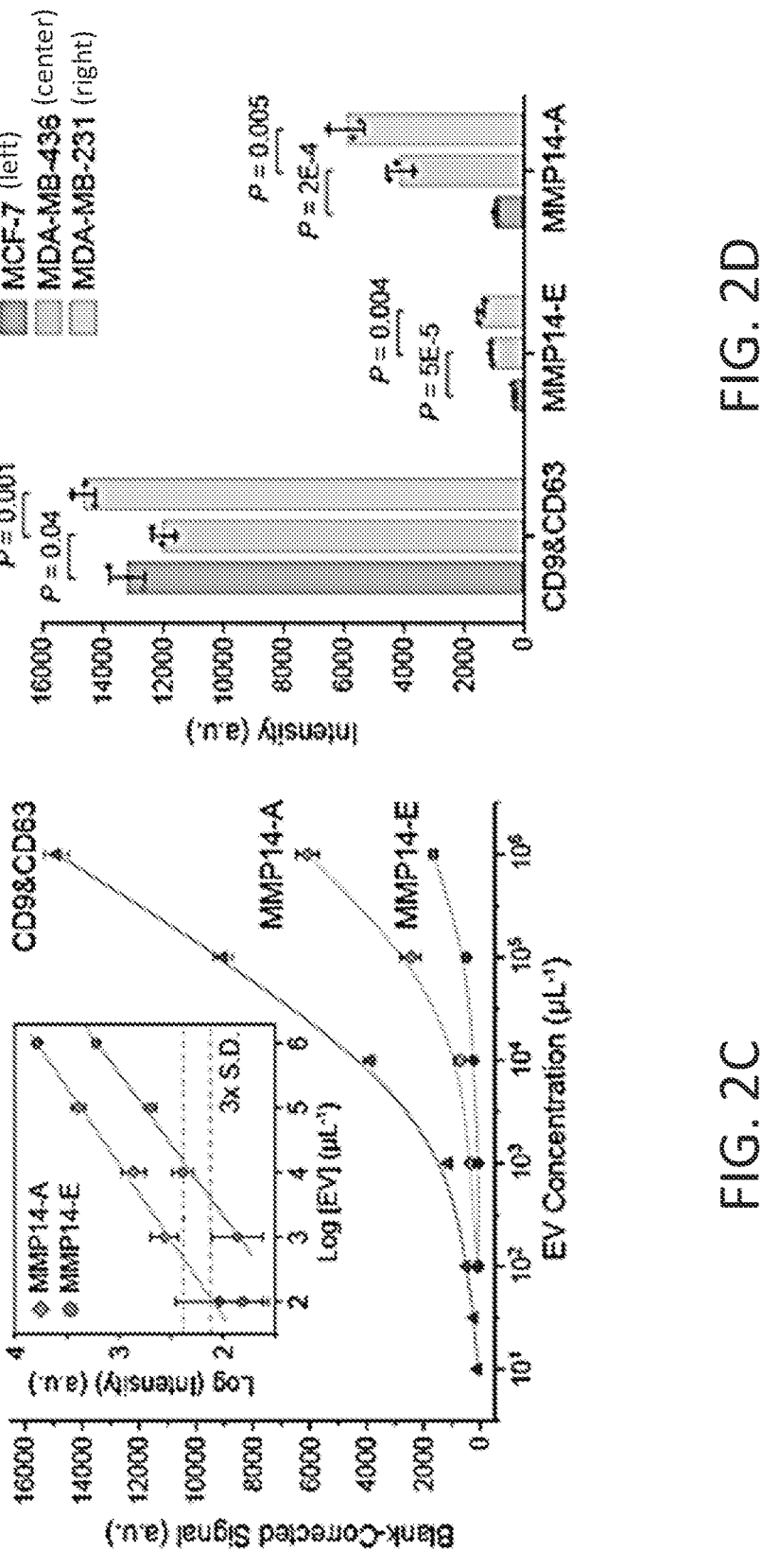

With the optimized assays, the analytical performance of the EV-CLUE technology was systematically calibrated. In addition to the MMP14 assays, a tetraspanin ELISA assay was assessed for quantifying the total sEV concentration by measuring the combined expression of CD9 and CD63. To this end, a serial dilution of UC-purified EVs from MDA-MB-231 cells was titrated, and a linear curve of the CD9 and CD63 expression as a function of the total EV concentrations measured by NTA was observed (FIG. 2C). The curve started to level off when the EV concentration decreased, yielding a low limit of detection (LOD) of ~16 EVs $\mu L^{-1}$ calculated by dividing three standard deviations of the background by the slope of the calibration plot. These cell line results support the CD9 and CD63 assay for quantitative detection of the total sEV concentration, which was further validated by the analysis of human plasma samples, as discussed below. Compared with the combined CD9 and CD63 expression, the calibration curve for the sEV MMP14 expression (MMP14-E) indicates that the MMP14+ sEVs accounted for a small fraction of the overall EV population and were detectable above a calculated EV concentration of ~5×10³ $\mu L^{-1}$ (FIG. 2C, inset). The MMP14 activity (MMP14-A) assay was observed to produce higher signals than the protein quantification, yielding a 10-fold lower LOD of ~5×10² EVs $\mu L^{-1}$. The EV-CLUE chip was then assessed for integrative molecular and functional phenotyping of tumor-derived sEVs using three breast cancer cell lines. The sEV MMP14 expression and activity assays with the equal EV inputs were able to differentiate the metastatic capabilities of the cells, with higher detection signals conferred by the activity assay (FIG. 2D). While providing the highest analytical sensitivity for sEV detection, the CD9&CD63 expression did not display clear correlation to the metastatic phenotypes. These findings highlight the necessity of highly sensitive detection of low-abundance, clinically relevant EV subtypes and suggest that the activity analysis could provide a sensitive means to probe pathological phenotypes of tumor-derived sEVs.

Detection of In Vitro Invasiveness of Isogenic Cell Line Models

Figure 3A:
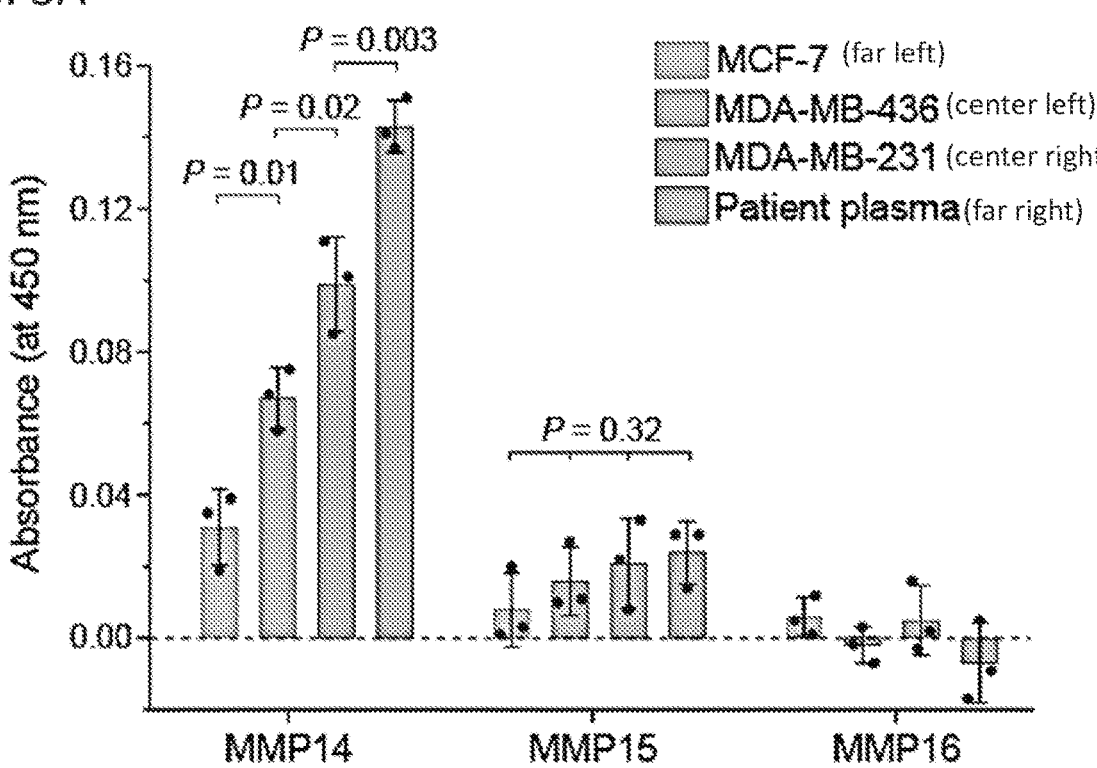
FIGS. 3A-3B show functional phenotyping of sEVs by the EV-CLUE technology detects tumor cell invasiveness.

As a proof-of-concept of potential clinical applications, the EV-CLUE technology was adapted for non-invasive measurement of tumor progression and metastasis using breast cancer as a disease model. A variety of MMPs have been identified in breast cancer-derived EVs, among which MMP-14 was the most frequently detected membrane-type MMP. Here quantification of MMP14 was attempted, along with another two major membrane MMPs, MMP15 and MMP16, which have been detected in breast cancer cell lines and tissues, but not in EVs. Using the standard microplate ELISA kits, MMP14 was readily detected in the samples of ~10⁹ EVs purified from three cell lines and the plasma of a metastatic breast cancer patient (FIG. 3A). The sEV MMP14 expression was observed to differentiate the variable metastatic potential of the cells and plasma sample, validating the chip-based measurements performed with less than 1/100 of the sample quantities (FIG. 2D). MMP15 expression was measured to be very low and unable to detect the metastatic cells, while MMP16 was essentially undetectable (FIG. 3A). Based on these and others' results, subsequent studies have been focused on only MMP14.

The EV-CLUE chip was assessed for integrative molecular and functional phenotyping of tumor-derived sEVs using isogenic cell lines. Two HuR CRISPR knockout (KO) clones were established from MDA-MB-231. HuR is an RNA-binding protein known to promote tumorigenesis and invasion. As verified by the Matrigel invasion assays, the invasiveness of MDA-MB-231 cells was largely reduced by knocking out HuR. It has been shown that downregulation of cellular MMP14 expression suppresses the invasiveness of metastatic MDA-MB-231 cells. However, WB analysis revealed that HuR KO does not impair the expression of MMP14 protein in the cells, but attenuates the amount of MMP14 protein carried by the secreted EVs. The findings together manifest the implication of EV-transported MMP14 in cell invasion. Therefore, while the mechanism of HuR-mediated regulation of EV transport of MMP14 remains to be elucidated, which is beyond the scope of this Example, this HuR KO model provides a useful approach to validate this technology and to specifically assess EV MMP14 as a marker of cell invasion. Using the EV-CLUE chip, the multiplexed molecular and functional phenotyping of EVs isolated from these isogenic cell lines was conducted in comparison with a lung metastatic subline of MDA-MB-231 (2LMP). The measured MMP14 phenotypes of sEVs, as opposed to the total sEV abundance, reflected the invasiveness of the parental and KO cell lines, and the measurements of MMP14 activity conferred a 2-3-fold increase in sensitivity than the protein quantification. Moreover, the results obtained with the EV-CLUE were quantitatively compared with the cell invasion assays. Regression analysis revealed a strong linear correlation between the sEV MMP14 proteolytic activity and the number of invading cells counted in the Matrigel invasion assays (Pearson's r=0.996, FIG. 3B). To assess the adaptability of this technology to other malignancies, a set of isogenic pancreatic cancer MIA PaCa2 isogenic cell lines were also tested, and consistent performance of the EV-CLUE chip for detecting in vitro cell invasiveness was observed. Overall, the findings suggest the potential of sEV MMP14 as a marker of tumor invasion and metastasis.

Non-Invasive Monitoring of Tumor Evolution In Vivo with Mouse Models

Figures 4A, 4B:
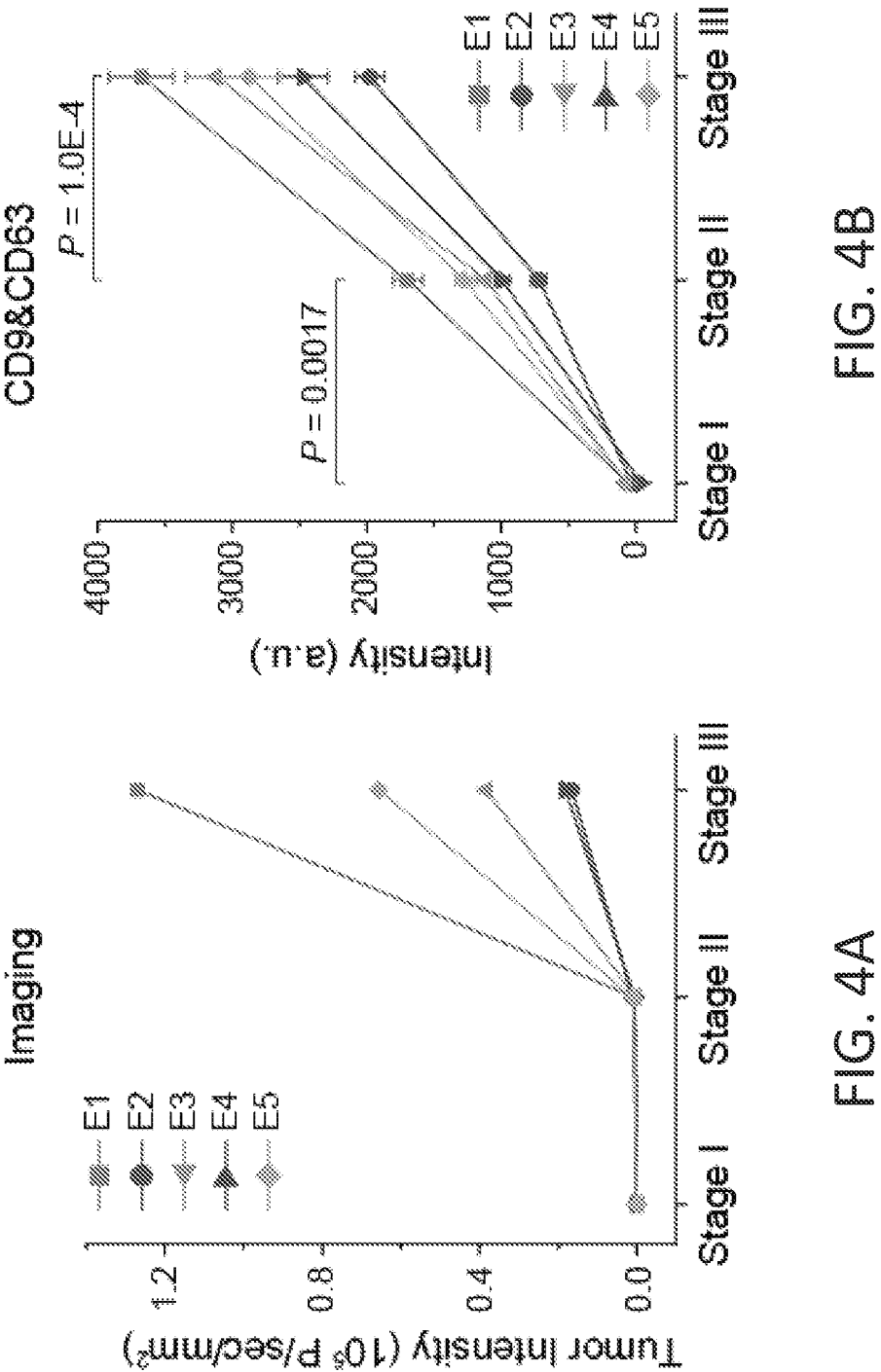
FIGS. 4A-4E demonstrate integrative sEV phenotyping for monitoring tumor development in vivo using an experimental metastasis model of human breast cancer. An experimental metastasis model in athymic nude mice was established by injecting $10^6$ 2LMP-Luc cells into the tail veins of 4-week-old female nude mice. Progression of the lung tumors was monitored by bioluminescent imaging.
Figures 4C, 4D:
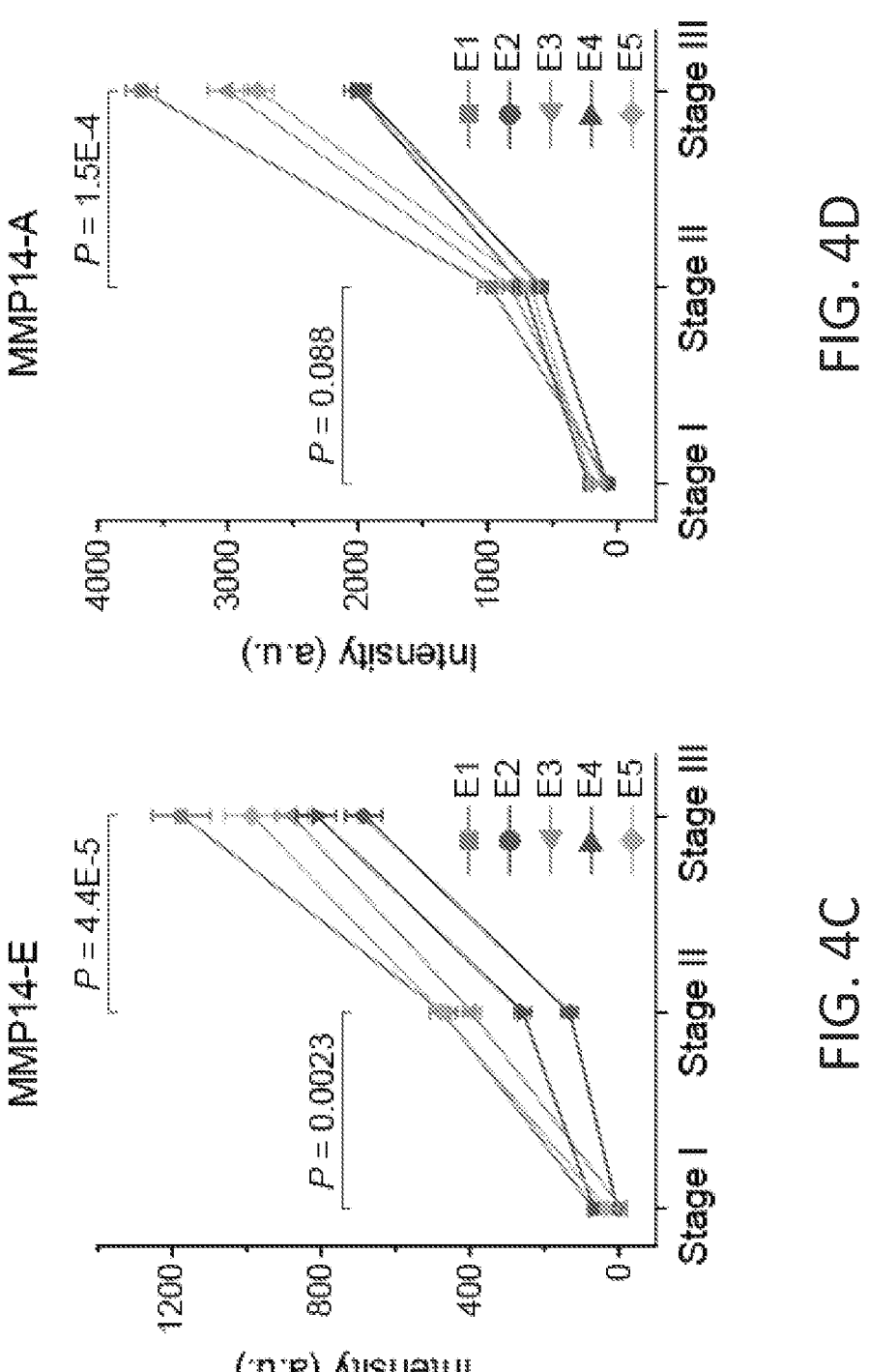
Figure 4E:
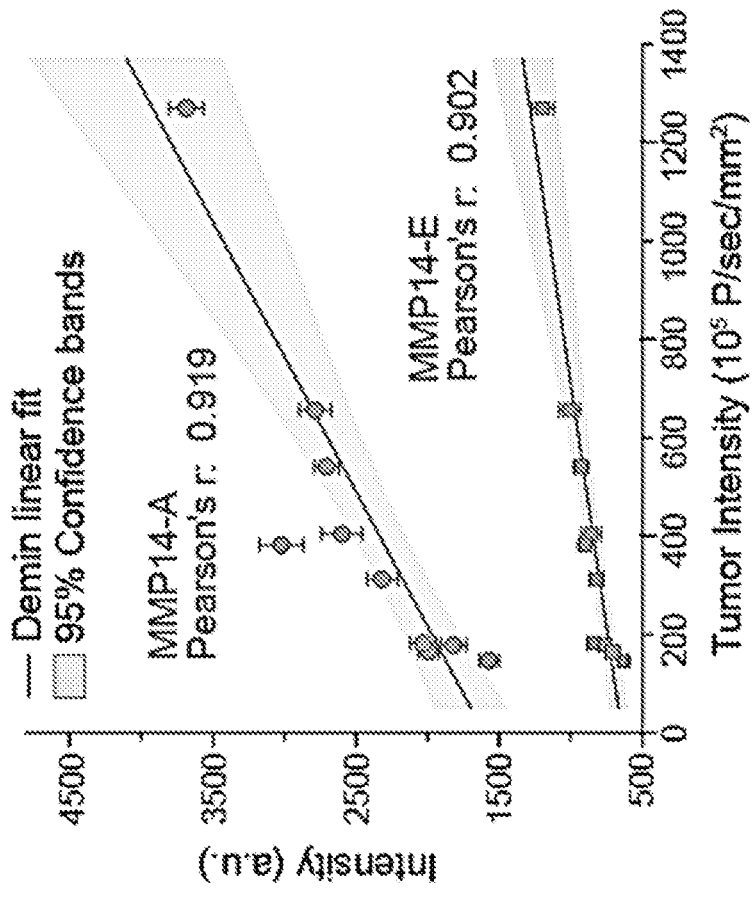

The feasibility of using the EV-CLUE technology for longitudinal monitoring of metastatic burden was first assessed using an experimental metastasis mouse model of human breast cancer. Since earlier steps in the metastatic cascade are bypassed, typically, experimental metastasis assays reduce the data variability and improve the statistical power per mouse, therefore providing a robust in vivo model for technology assessment. In this model, $10^6$ 2LMP-Luc cells (luciferase-expressing lung metastatic subline of MDA-MB-231) were injected into the lateral tail veins of athymic nude female mice. The development and growth of tumors, primarily at lungs, were monitored by imaging twice a week. FIG. 4A shows the results of tumor intensity plots acquired for the same mice at three stages: I) prior to inoculation; II) initial detection of early metastasis; III) close to moribund with extensive lung metastases. ~50 µL blood was repeatedly collected from each mouse at the three stages to prepare plasma for the microfluidic analysis. The antibodies for specific immunocapture and molecular analysis of human-derived sEVs in blood plasma of the xenografted mice were identified and validated. With these optimized assays, multiparametric analysis of human cancer-derived sEVs was demonstrated directly in 6 µL mouse plasma per run. As presented in FIGS. 4B-4D, chip analysis of the total abundance, MMP14 expression, and MMP14 activity of sEVs enables longitudinal monitoring of progressive tumor development in individual mice (n=5, Data file 51). To quantitatively evaluate sEV MMP14 as a marker of tumor burden, the measured sEV phenotypes were compared with the tumor intensity measured for 10 xenografted mice at the Stage III (FIG. 4E). Both sEV MMP14-E and -A were found to correlate well with the tumor intensity at the Stage III, and the activity analysis provided a higher sensitivity, the same as observed in the sEV phenotyping of cell lines as described above.

Figure 5A:
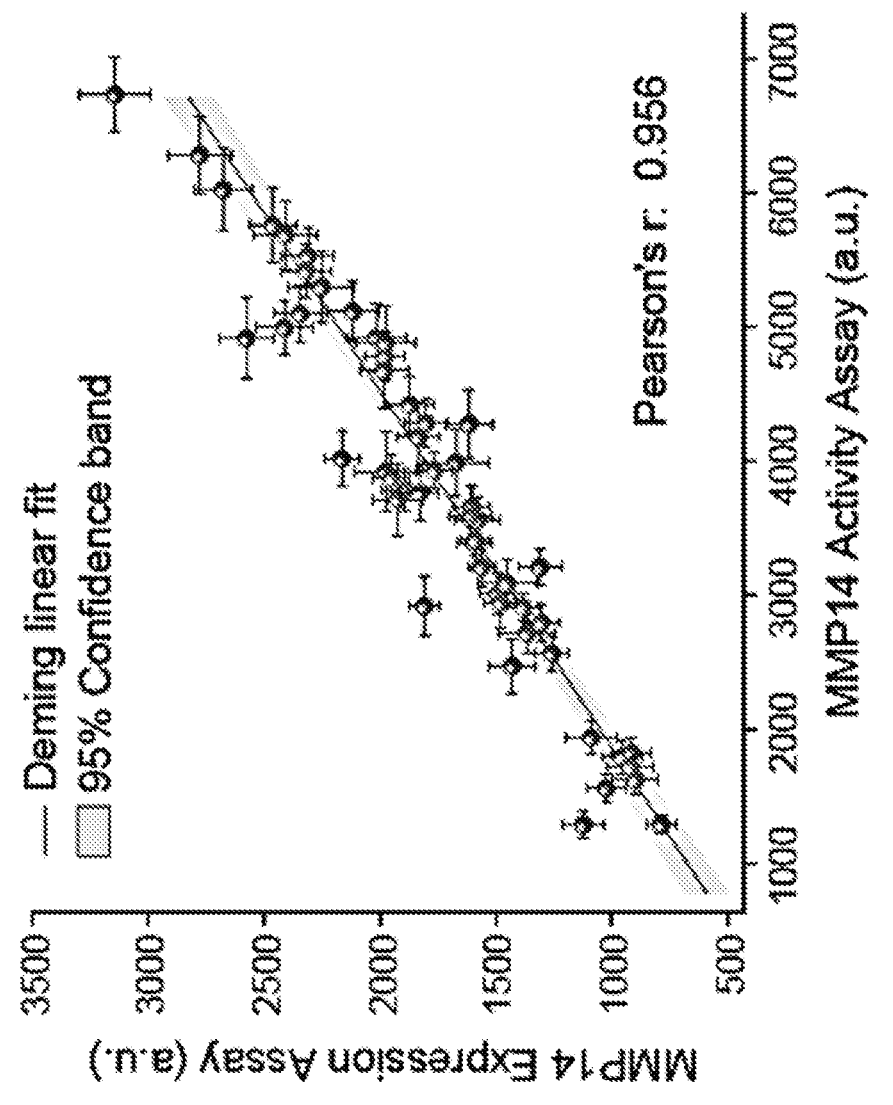
FIGS. 5A-5D show longitudinal monitoring of tumor evolution in a spontaneous breast cancer metastasis model.

To further assess the biomedical applicability of this technology, the in vivo mouse studies were extended to a spontaneous metastasis model that includes all the steps in the pathogenesis of metastasis to closely recapitulate the clinical reality. In this orthotopic mouse model, $0.5 \times 10^6$ mouse 4T1-Luc breast cancer cells were injected into the #4 mammary fat pad of 4-week-old female BALB/c mice (n=16). Primary tumor growth was assessed by caliper measurements of the mammary xenografts to calculate tumor volume using the modified ellipsoidal formula of Faustino-Rocha, A. et al. *Lab Animal* 42, 217 (2013), while the development of metastases was monitored by bioluminescence imaging. Meanwhile, repeated collection of ~50 µL blood from tail veins of each mouse was conducted before and after inoculation. The mice were sacrificed at the end of Week 5, 12 out of which were found to develop metastases at lungs. Multiplexed analysis of the longitudinal plasma samples collected from each mouse was performed, which was enabled by the EV-CLUE technology requiring only a few µL sample input. As opposed to the experimental model, the total sEV abundance did not appear to be a potent indicator of tumor development in the spontaneous model. This discrepancy is attributed to the fact that the experimental metastasis assay probes human xenograft-derived sEVs against the background of mouse sEVs, while in the spontaneous model the total sEV assay also detected a vast quantity of wide-type sEVs which masked the dynamics of tumor-derived vesicles. The sEV expression and activity of tumor-related MMP14 were observed to increase along with tumor growth and metastasis in individual mice. Statistical analysis showed that this method was able to detect a significant increase in the population means of the MMP14 markers over one-week tumor development, e.g., P=0.003 for MMP14-E and P=6.8E-4 for MMP14-A in Week 5. Notably, while the single-mouse longitudinal sEV analysis revealed notable increase in sEV MMP14 expression and activity in a number of mice over certain time intervals (e.g., Week 4), analysis of the population means showed no significant difference (Week 4, MMP14-E: P=0.18, MMP14-A: P=0.26), which could be attributed to the large inter-individual heterogeneity observed by this method. Regression analysis of all data measured for 16 mice resulted in a strong linear correlation between the expression and activity of sEV MMP14 (Pearson's r=0.956, FIG. 5A). These results, combined with the in vitro cell analysis and the experimental metastasis assays as described above, validate the technology for highly sensitive and specific molecular and functional profiling of tumor-derived sEVs.

Figure 5B:
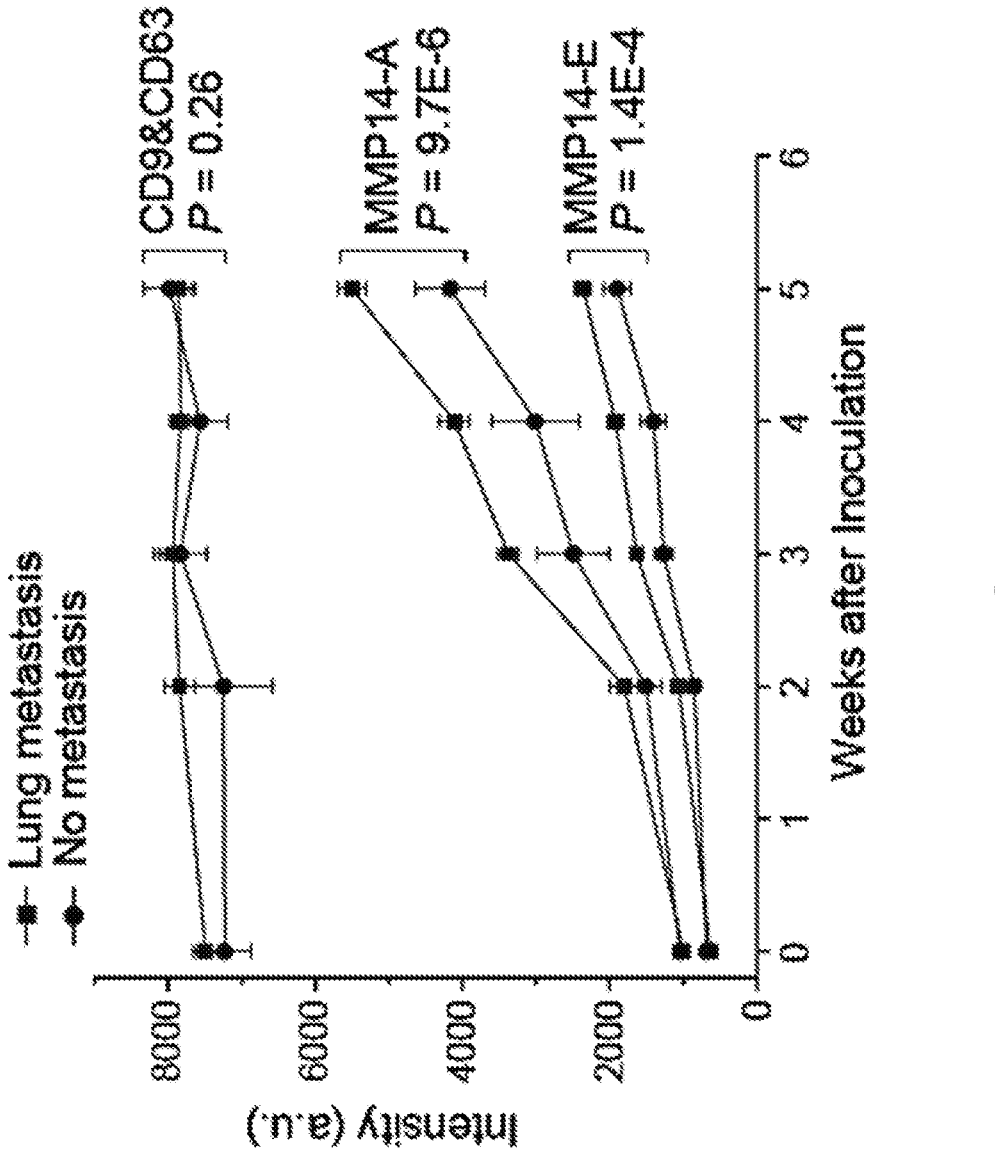
Figure 5C:
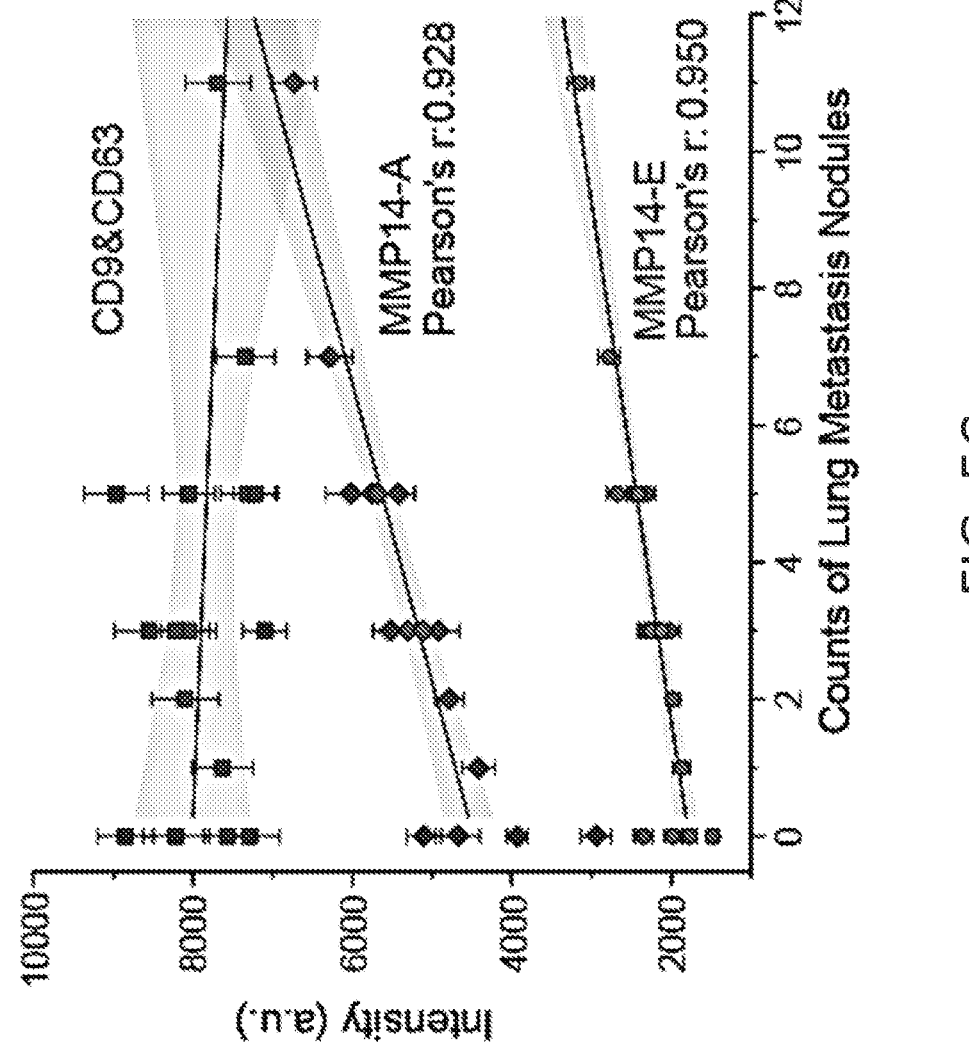
Figure 5D:
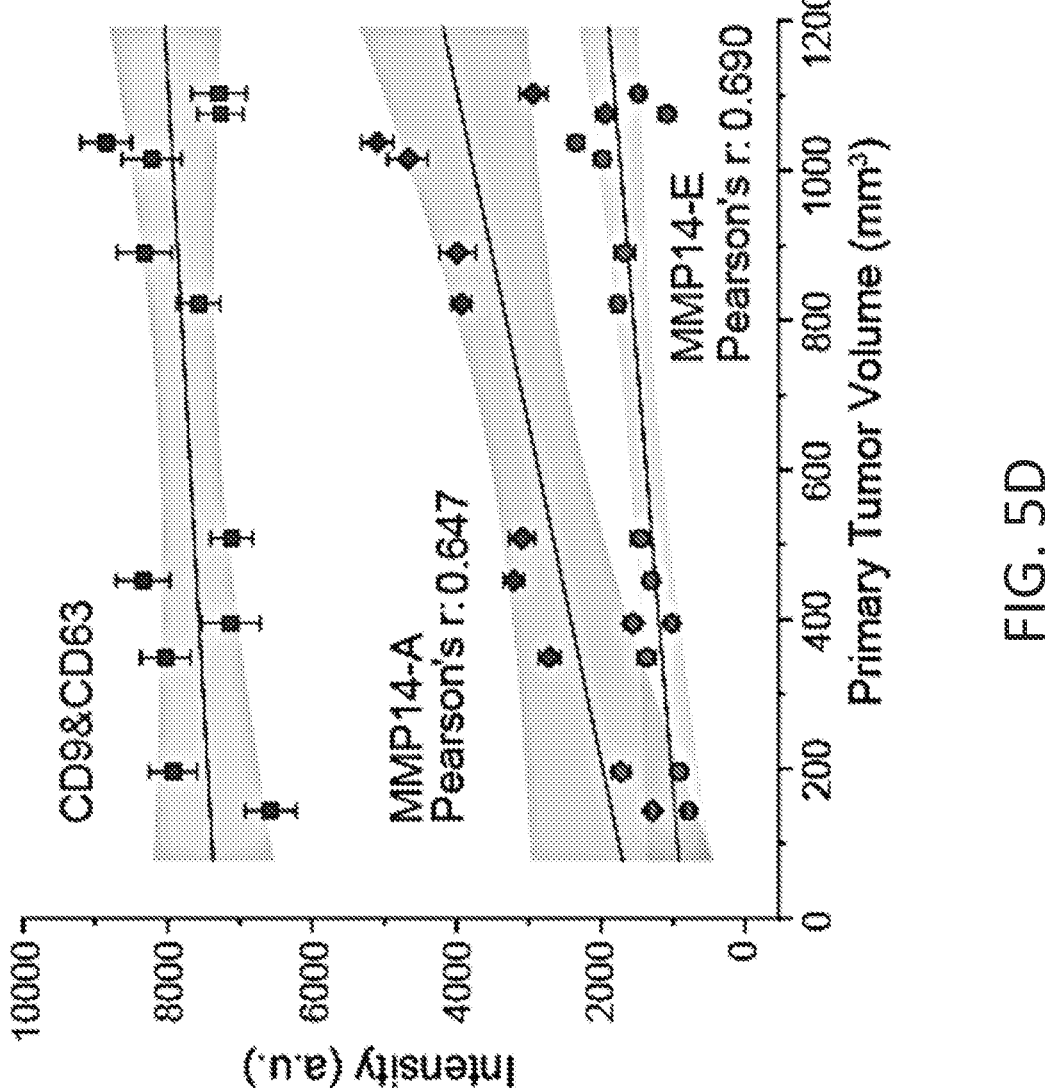

Next, the longitudinal sEV measurements were compared between the subgroups of mice which developed primary tumor only (n=4) and with lung metastasis (n=12). In contrast to the total sEV concentration (P=0.26), both sEV MMP14 expression (P=1.4E-4) and activity (P=9.7E-6) exhibited a significantly faster overall increase rate in the mice developing metastases than those with only primary tumors, and the activity assay outperformed the expression assay for detecting the tumor burden in vivo (FIG. 5B). Statistical comparisons at individual time points also showed that monitoring the change in sEV MMP14 activity provided better statistic power to differentiate two mouse subgroups than the MMP14 expression, suggesting the potential of the functional activity of sEVs for detection of tumor metastasis. To further assess the correlation between the sEV phenotypes with metastasis, the sEV results were compared with the number of lung metastasis nodules measured at Week 5 (FIG. 5C) and the volume of primary tumor measured from Week 2 to 5 for the 4 mice which only developed primary tumors (FIG. 5D). Consistently, the sEV MMP14 markers exhibited significantly stronger correlation with the lung metastases (Pearson's r=0.950 for MMP14-E and 0.928 for MMP14-A) than the mammary xenografts (Pearson's r=0.690 for MMP14-E and 0.647 for MMP14-A). Collectively, the spontaneous metastasis model studies should further verify the feasibility of sEV MMP14 phenotypes as a potent biomarker of aggressiveness and metastatic potential of a tumor and the superior analytical performance of the nano-engineered chip. It was also demonstrated that the EV-CLUE technology enables minimally-invasive, real-time monitoring of the dynamics of tumor development in individual mice.

Clinical Analysis of Breast Cancer Patient Cohorts

Figure 6A:
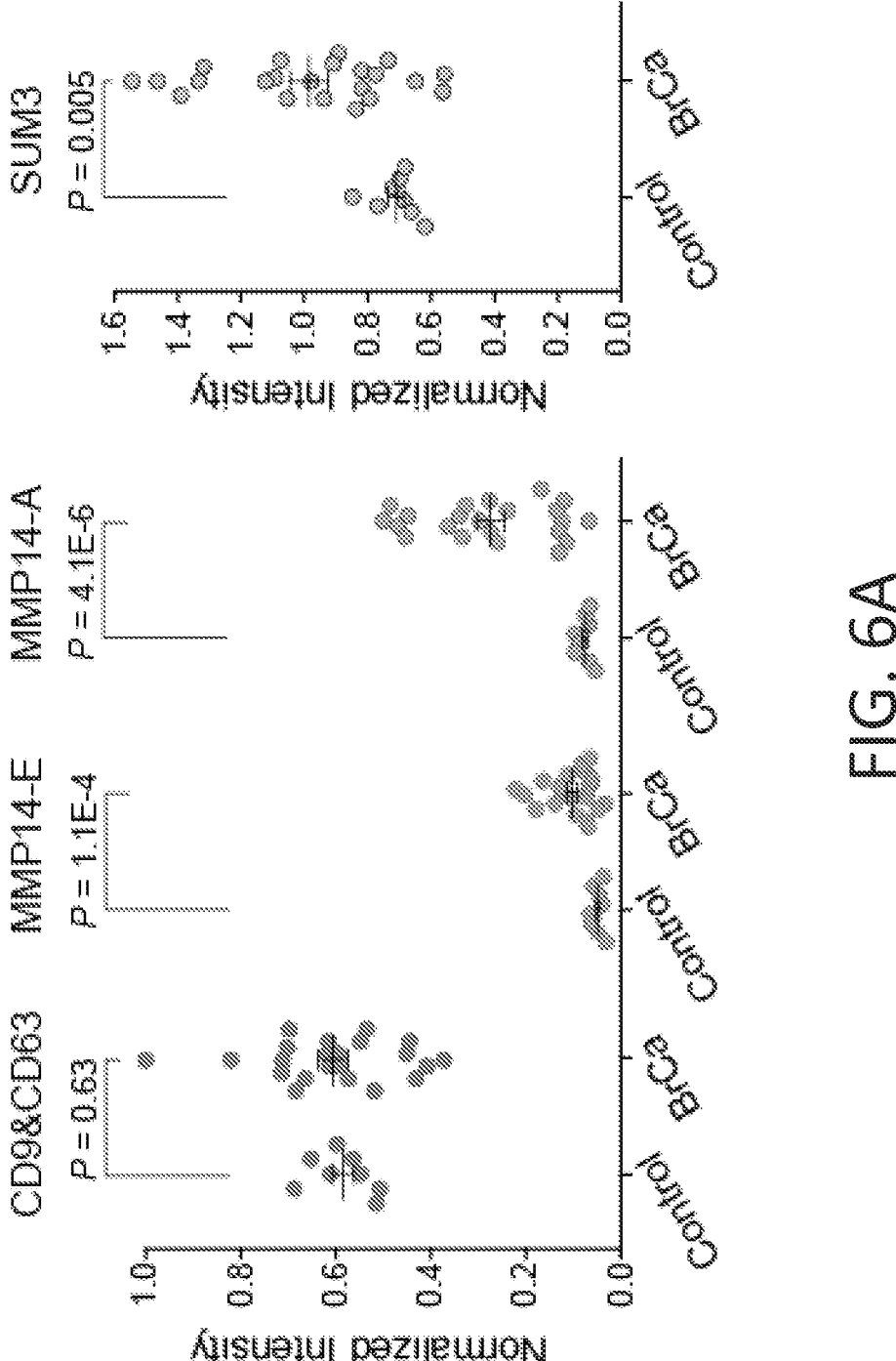
FIGS. 6A-6D demonstrate integrative sEV phenotyping of human breast cancer (BrCa) in a training cohort.

The EV-CLUE technology was next assessed for clinical applications to human malignancies, using plasma samples collected from a training cohort of stage 0-III breast cancer patients (n=22) and age-matched non-cancer controls (n=8). As proof-of-concept study of the feasibility of this method for molecular diagnosis and monitoring of disease progression, the patient cases involved three groups of distinct clinical stages: pre-invasive ductal carcinoma in situ (DCIS, n=8), non-metastatic invasive ductal carcinoma (IDC, n=7), and locally advanced IDC with lymph nodes metastases (n=7). Each breast cancer type includes diverse histological and molecular subtypes, including TNBC, to represent the tumor heterogeneity. Measurements of individual sEV markers for each subject were summarized, and the SUM3 signature was defined by the unweighted sum of three markers. The detection of sEV MMP14 was verified by the standard WB analysis of UC-purified EVs, which detected high expression of CD81 in both control and patients and low-abundance sEV MMP14 in patients with a notably elevated abundance in the metastatic case. As shown in FIG. 6A, the total sEV concentration exhibited no significant difference between the cancer and control groups (two-tailed Mann-Whitney U test, P=0.63), while the sEV MMP14 markers were able to differentiate the two groups (P=1.1E-4 for MMP14-E and P=4.1E-6 for MMP14-A), in spite of large inter-individual variations. It is noted that multiparametric combination with the functional activity marker improves the performance of molecular phenotyping of sEVs for cancer detection, e.g., P=1.0E-5 for SUM2 (MMP14-E+MMP14-A) versus P=1.0E-5 for MMP14-E, and P=0.005 for SUM3 versus P=0.27 for SUM1 (CD9&CD63+MMP14-E) (FIG. 6A).

The diagnostic metrics of the biomarkers were evaluated individually and in combinations using a multivariate receiver operating characteristic (ROC) curve analysis strategy based on linear discriminant analysis (LDA). The training set data was processed by LDA to create a discriminant function model for classification of two groups of samples. The predicted probabilities yielded from this binary classification procedure were used as the single test variable for ROC analyses. Among three markers, sEV MMP14 activity showed the best diagnostic performance for the training cohort with 0.977 (95% CI, 0.845-1) area under the curve (AUC), 95.5% sensitivity (95% CI, 77.2-99.9%), 100% specificity (95% CI, 63.1-100%), and 96.7% accuracy (95% CI, 82.8-99.9%). Evaluation of various combinations of the markers showed that multivariate detection with the marker panels affords comparable or better diagnostic power than univariate detection using single SUM signatures, e.g., COM3 (0.977 AUC, 100% sensitivity, 87.5% specificity, 96.7% accuracy) versus SUM3 (0.830 AUC, 81.8% sensitivity, 87.5% specificity, 83.3% accuracy). While providing almost the same performance as the sEV MMP14 activity for diagnosis of cancer against control, the three-maker panel COM3 was observed to improve the classification of patients at variable disease stages, as delineated below.

Figure 6B:
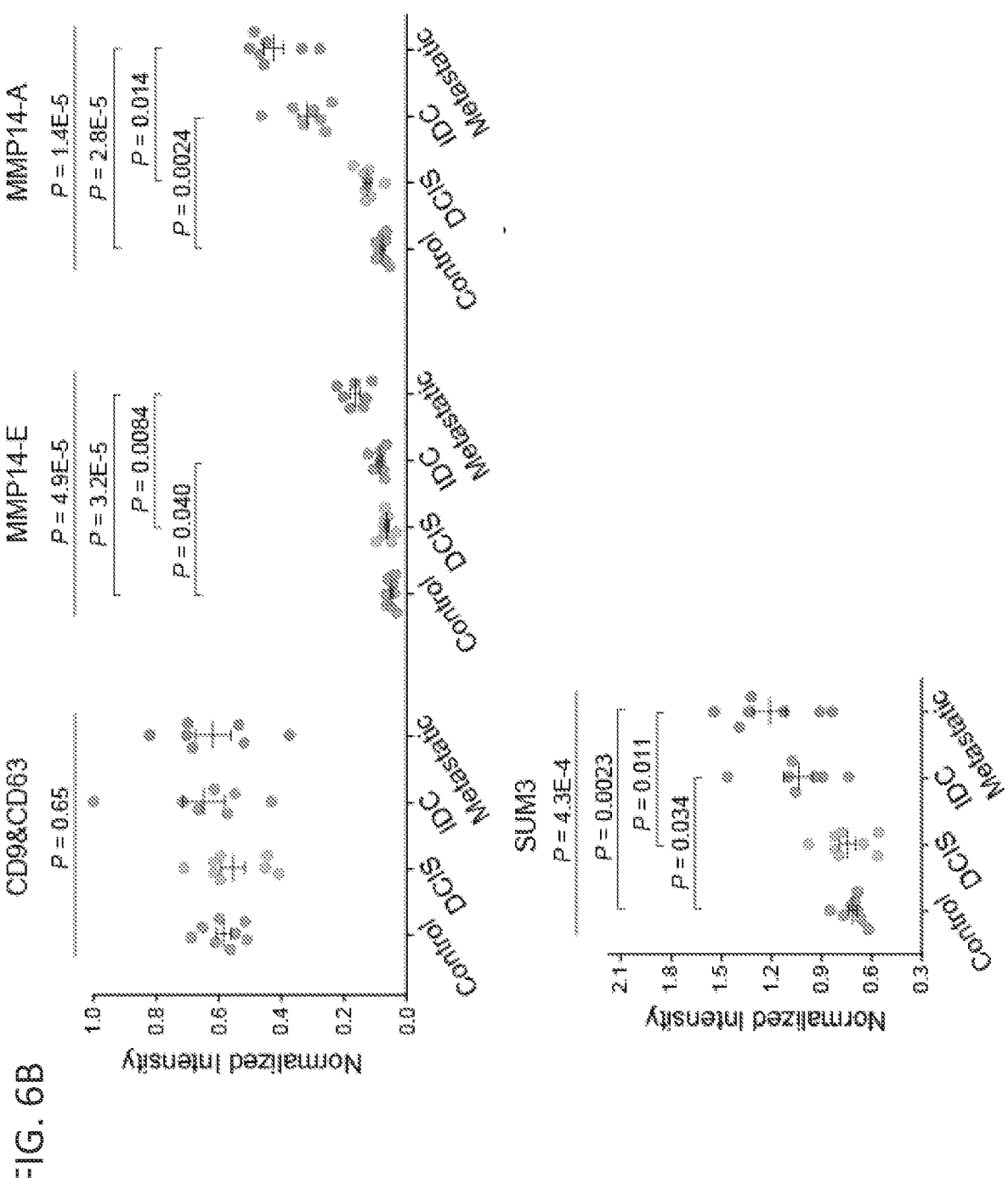
Figure 6C:
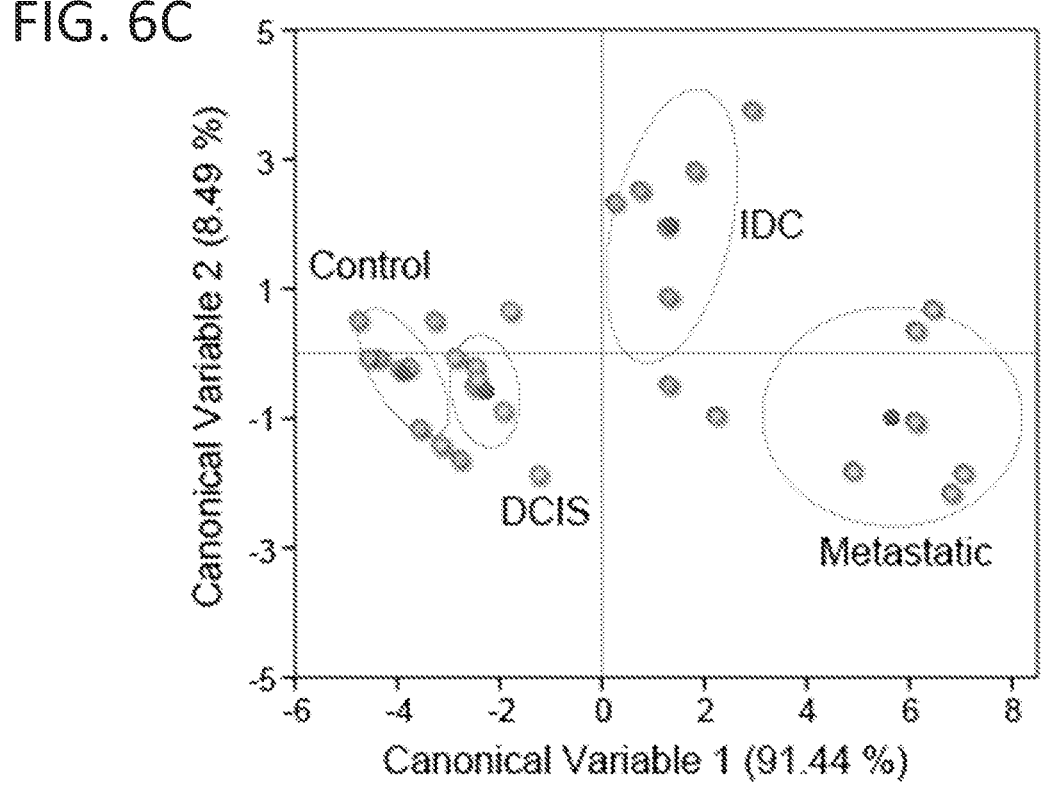
Figure 6D:
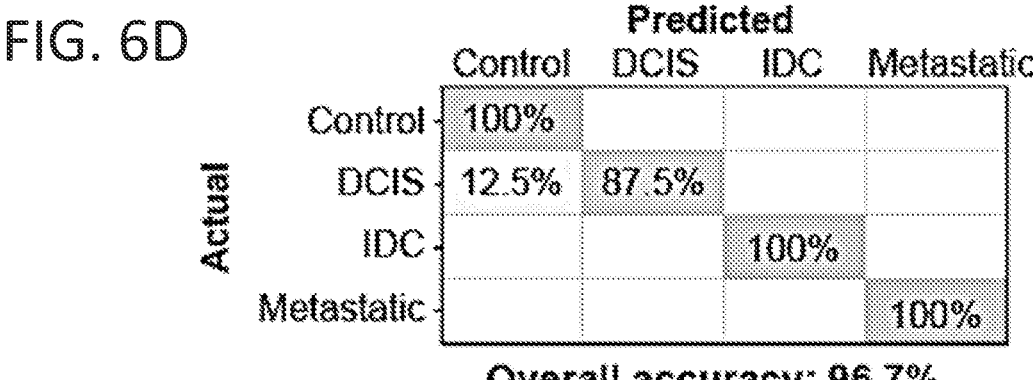

FIG. 6B depicts the assessment of this method for detecting the controls and three subgroups of patients: pre-invasive DCIS, non-metastatic IDC, and locally metastatic IDC. An overall significant increase was observed in the sEV MMP14 expression (Kruskal-Wallis one-way ANOVA, P=4.9E-5) and activity (P=1.4E-5) and the SUM3 signature (P=4.3E-4), along with the progressive disease stages. Post-hoc Dunn's pairwise multiple comparisons test revealed significant differences between three group pairs, i.e., control versus IDC (MMP14-E, P=0.04; MMP14-A, P=0.0024), control versus metastatic IDC (MMP14-E, P=3.2E-5; MMP14-A, P=2.8E-5), and DCIS versus metastatic IDC (MMP14-E, P=0.0084; MMP14-A, P=0.014) (FIG. 6B). Moreover, the sEV MMP14 markers were able to discriminate the combined group of invasive and locally advanced IDC cases from the control or pre-invasive DCIS group. To further explore the capacity of this method for diagnosis and stratification of breast cancer, discriminant analysis of the sEV phenotypes was conducted individually and in combination for classification of the training cohort. The quadratic method was chosen to generate the discriminant models as the equality test of within-group covariance matrices failed. The classification results obtained with the 3-marker panel COM3 were visualized in FIG. 6C. It was seen that the discriminant analysis of COM3 correctly classifies individual subjects into the four groups except for one DCIS case misidentified as the control. The classification results were quantitatively presented as a confusion matrix (FIG. 6D), showing an overall accuracy of 96.7% (95% CI, 82.8-99.9%) which was better than that of the sEV MMP14 activity alone (86.7%). Such improvement demonstrates the advantage of the multiparametric sEV marker panel versus single markers for multi-class diagnostics. To further characterize the effectiveness of this method to discriminate the subgroups, the scores of each subject were plotted for the first two canonical variables computed from the discriminant analysis (FIG. 6C). It was clearly visualized that the training samples were classified into four groups with notably better separation among the patient groups at progressing disease stages. A correlation circle was also created by projecting the input variables (i.e., sEV markers) in the factors space. It shows strong positive correlation of the sEV markers to the first canonical variable that highlights their contribution to the accurate disease classification. Interestingly, the correlation circle also reveals a weak but positive correlation of the CD9&CD63 expression to the canonical variables, which explains its role in improving the accuracy of the multi-class diagnostics when combined with the sEV MMP14 markers.

Figure 7A:
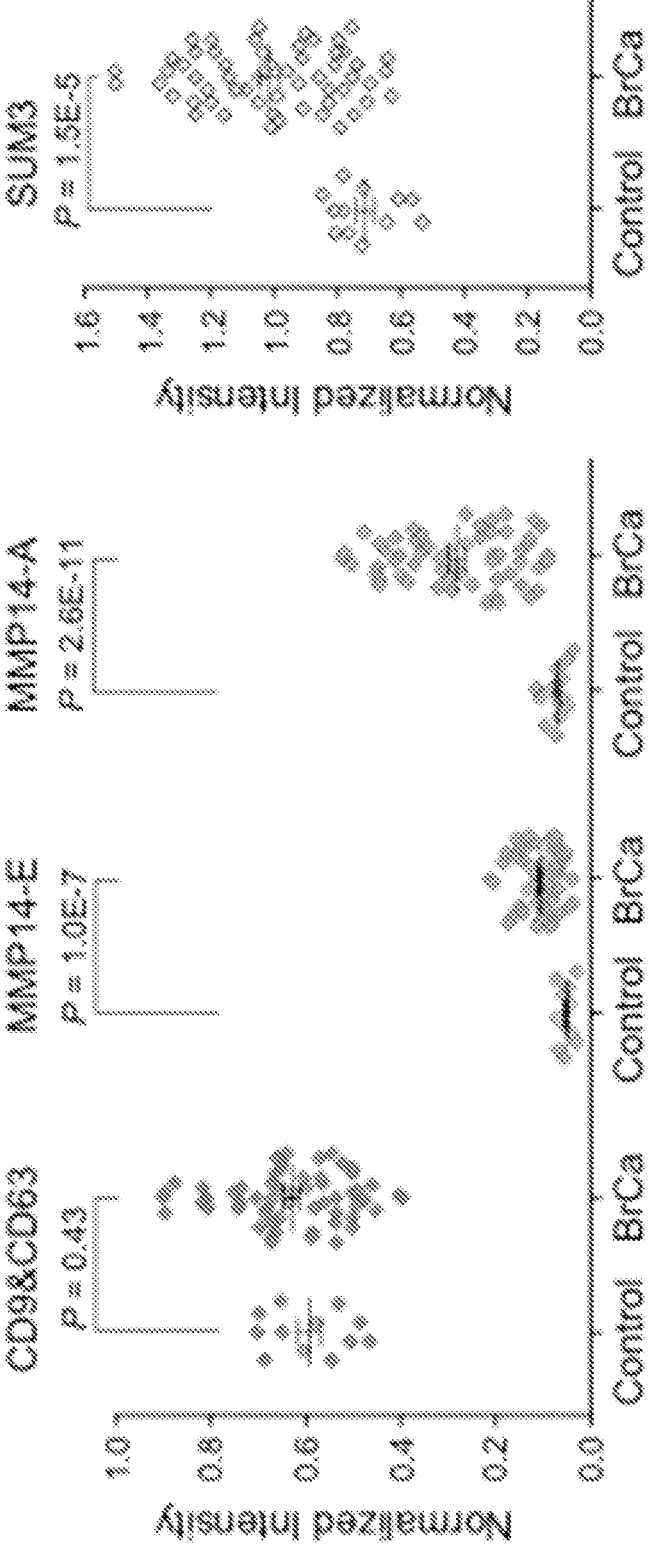
FIGS. 7A-7D demonstrate validation of integrative functional sEV phenotyping for non-invasive diagnosis and monitoring progression and metastasis of BrCa.

The EV-CLUE technology was further applied to measure an independent validation cohort of age-matched cancer-free controls (n=12) and breast cancer patients (n=58) involving 18 DCIS, 20 non-metastatic IDC, and 20 locally advanced breast cancer with lymph nodes metastases. Correlation analyses of the sEV MMP14 expression and activity data found no significant difference between the training and validation cohorts (P=0.46) using one-way analysis of covariance (ANCOVA) and yielded a high Pearson coefficient of 0.956 for two cohorts combined, indicating the adaptability of the assays to specific and reliable analysis of clinical plasma samples. The patients with various histological and molecular subtypes were distinguished from the controls by the measured sEV MMP14 expression (two-tailed Mann-Whitney U test, P=1.0E-7) and activity (P=2.6E-11, FIG. 7A). The validation set data were fed into the discriminant function model established from LDA of the training cohort to test its validity for clinical diagnosis. To this end, the post probabilities predicted for the validation cohort without known a priori disease state were used to conduct ROC analysis. Consistent diagnostic performance of three sEV parameters was observed between the training and validation cohorts in terms of AUC (e.g., 0.926 vs. 0.930 for MMP14-E and 0.977 vs. 0.986 for MMP14-A) and accuracy (86.7% vs. 85.7% for MMP14-E and 96.7% vs. 92.9% for MMP14-A).

Figure 7B:
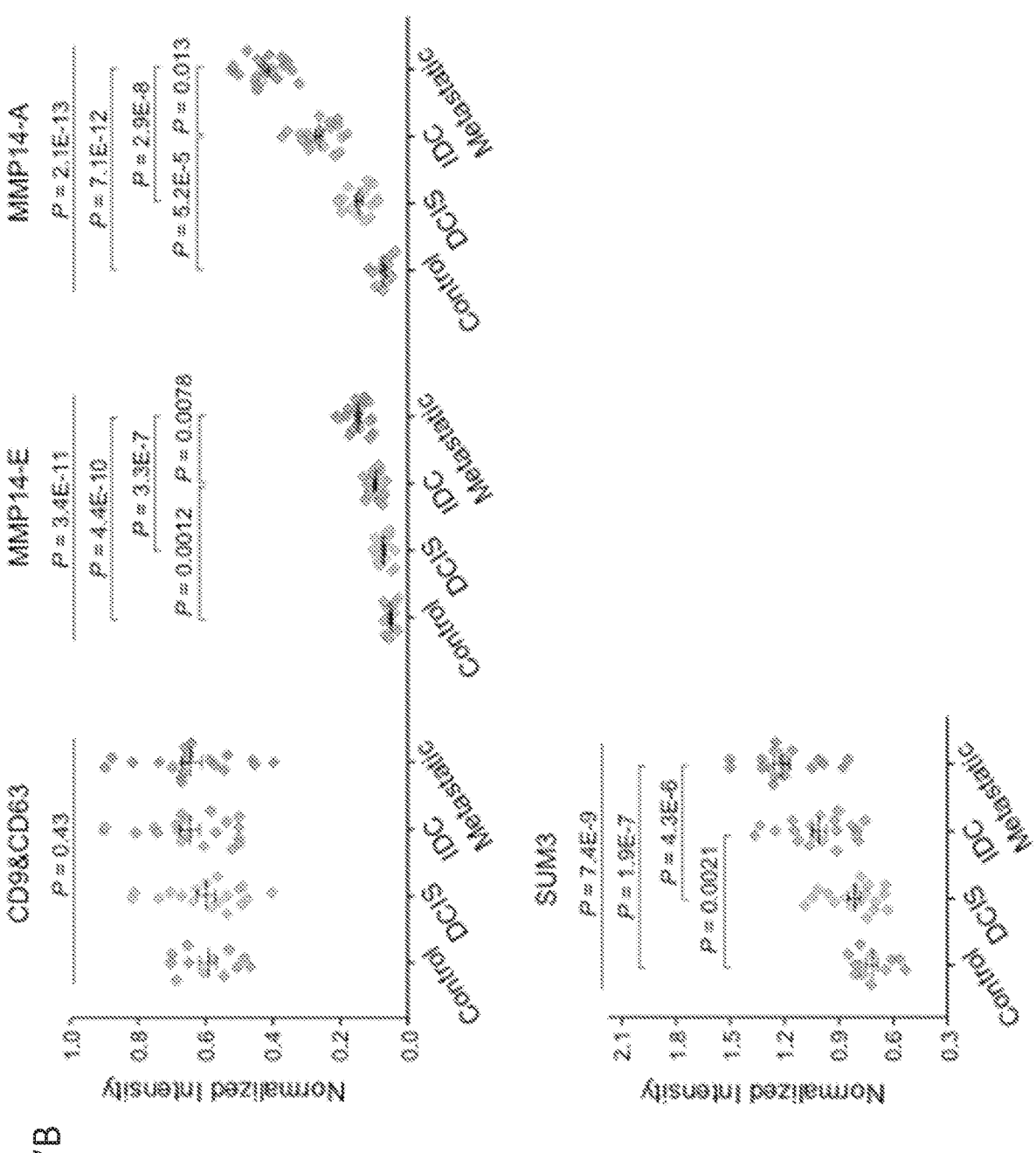
Figure 7C:
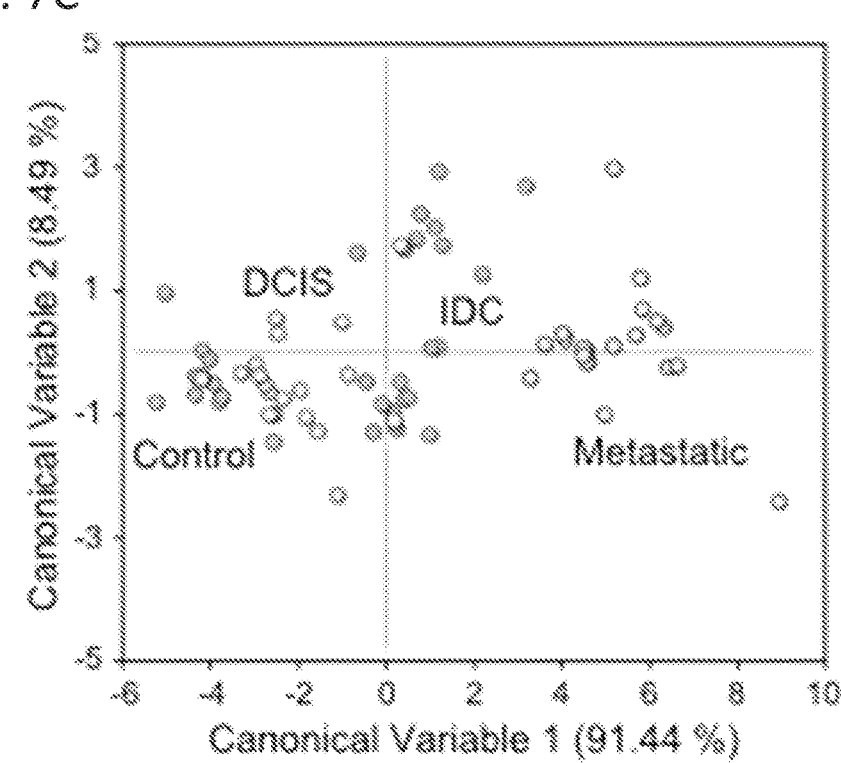

Using different statistical approaches, the validation cohort data were then evaluated for detecting the progression stages of breast cancer. Compared to the training cohort, a considerable improvement in differentiating the four groups of subjects in the validation cohort was observed with the Kruskal-Wallis one-way ANOVA followed by the Post-hoc Dunn's multiple comparisons test (FIG. 7B). In particular, as opposed to the training cohort, here significant increases in the sEV MMP14 expression (P=0.0078) and activity (P=0.013) were detected in the metastatic group versus the localized IDC group. Enhanced statistic distinction between the combined malignant group and the control or DCIS group in the validation cohort was also observed when probing the MMP14+ sEVs. Such improvement could be attributed to the larger sample size of the validation cohort that reduces the sampling variances. Classification analysis of the validation cohort data was then performed with the discriminant function model derived from the training cohort to test its reliability for multi-class diagnosis of breast cancer. As summarized in confusion matrices, the classification accuracy for the training and validation cohorts was consistent (e.g., 86.7% vs. 81.4% for MMP14-A). Among the biomarker combinations tested here, discriminant analysis of COM3 yielded the best classification performance, as detailed in FIGS. 7C, 7D. It is noted that all the IDC and metastatic IDC cases in the validation cohort were correctly detected and only two non-invasive DCIS cases were misclassified to be invasive, leading to an overall accuracy of 92.9% (95% CI, 84.1-97.6%, FIG. 7D). This observation was also reflected in the canonical score plot which displays distinct separation among the four groups in the validation cohort in the 2-dimensional discriminant factor space defined by the training samples (FIG. 7C).

The nanochip-based integrative phenotyping of circulating sEVs was systematically validated by the measurements of the same samples with a variety of gold standard approaches. EVs were isolated by UC from a subset of control and BrCa samples randomly selected from the training and validation cohorts (n=10 for each subgroup) and characterized by the NTA and Bradford assays. A summary of the NTA results showed the variable mean diameters of ~100-160 nm with the major size distribution ranging from ~60 to 400 nm. To assess the CD9 and CD63 assay for quantifying the total EV concentration in human plasma, the nanochip signals were plotted against the EV abundance counted by NTA for these 40 plasma samples. Regression analysis resulted in a strong linear correlation between the two methods (Pearson's r=0.931). This plasma analysis together with the cell line studies (FIG. 2C) should demonstrate the tetraspanin-based assay as a means to quantitatively estimate the abundance of circulating EVs. It should be noted that the applicability of this method may be limited by the heterogeneous tetraspanin expression on EVs and thus needs to be validated in individual cases. The EV numbers and sizes measured by NTA were compared across the control and BrCa groups, which showed no significant difference (P=0.53 and 0.47, respectively). The total EV protein expression measured by the Bradford assay was seen to detect the difference between the control group and each of the patient groups, but not among the patient groups. Compared to these measurements of general EV properties, the nanochip method targeting tumor-associated markers on sEVs greatly augments diagnostic performance.

To further demonstrate the advantageous performance of this technology, comparison to standard microplate ELISA was attempted for targeted analysis of sEV MMP14 marker. A set of 60 samples (n=15 for each subgroup) from the two cohorts were measured by a commerically available microplate EV ELISA kit. This standard assay yielded a similar sEV MMP14-E pattern to the nanochip analysis, but with much less signal intensity. Comparing the data obtained with the two methods, a strong linear correlation (Pearson's r=0.991) was revealed at the high-concentration range, and the lower concentrations were only detectable with the nanochip method. ROC analysis showed that the nanochip analysis of the sEV MMP14 expression improved the diagnosis of the BrCa patients from the controls than the standard ELISA (AUC: 0.934 vs. 0.800). Moreover, this technology was able to differentiate the individual groups of control and DCIS combined, IDC, and metastatic cases, while the standard ELISA assay only detected the metastatic group. These comparative results further support the ability of this technology to enhance the diagnostic performance while reducing the sample consumption and assay time by a factor of >5, owing to its vastly improved detection sensitivity. Finally, to examine the potential of plasma-borne sEVs as the liquid biopsy of solid tumors, breast tissues from four of the BrCa patients were assayed with standard H&E and immunohistochemistry (IHC) staining. The expression of MMP14 was barely to weakly detectable in the tumor tissues from the two DCIS patients. For the other two patients with IDC and metastatic IDC, respectively, there was an apparent increase in staining intensity with weak to moderate MMP14 expression observed in the carcinoma compartment of the primary tumors. For comparison, the tumor-adjacent normal breast tissue available from the same IDC patient was stained, which displayed the absence of detectable MMP14 expression. These IHC assay results appear to support the correlation between the biomarker profiles of circulating sEVs and solid tumors, and thus the potential applications of sEVs as a non-invasive surrogate biopsy of tumors. Collectively, the studies of clinical cohorts show the adaptability of this integrative molecular and functional sEV phenotyping technology to improve post-diagnosis surveillance of cancer status for early detection of tumor invasion or metastasis.

Discussion

Nanoengineering of microdevices provides a proven strategy to effectively augment the sensitivity, accuracy, and speed of bioanalysis via constructing multi-scale systems to combine the advantages of micro- and nano-scale flow dynamics and biochemical reactions. Nanoengineering of biosensors is usually accomplished by top-down nanofabrication using standard nanolithography or other sophisticated physical/chemical methods, as well as by bottom-up surface patterning with nanomaterials. These methods often produce 2D nanofeatures with respect to the dimensions of microscale sensors. Moreover, a key barrier toward practical nanomanufacturing arises from the limited scalability and standardizability of these methods which often involve expensive, sophisticated facilities and labor-intensive fabrication procedures. Earlier studies to address these limitations presented a microchannel-based µCSA strategy for bottom-up 3D nanoengineering of microelements to immensely improve the sensitivity of protein profiling of sEVs. (Zhang, P. et al., *Chem Sci* 10, 5495-5504 (2019); Zhang, P. et al. *Nat Biomed Eng* 3, 438-451 (2019).) While enabling simple and high-quality 3D nanopatterning, this prototyping method utilizes manual processes, which can result in high cost, batch-to-batch variation in yield, and limited compatibility with mass production.

Here the CSA-based multiscale engineering strategy was further expanded by developing a general, high-resolution colloidal inkjet printing method using an industrial-grade material printer. Inkjet printing is cost-effective, flexible, and scalable. However, these techniques have three major limitations that need to be overcome for these applications. First, they are often limited to low-resolution printing of 2D colloidal patterns of a few micron thickness. Increasing ink concentration and jetting droplet volume can print thicker materials. However, concentrated particles can easily clog small inkjet nozzles required for high-resolution printing, and the use of large jetting droplets also limits the printing resolution. Second, largely uncontrolled solvent evaporation results in uneven distribution of nanoparticles during CSA and even broken, irregular patterns, making it challenging to print large-scale, continuous features. Lastly, to better control the geometry and quality of printed patterns, current techniques rely on delicately tuning surface modifications and ink composition to adjust the interactions between surface wetting and evaporation-driven CSA. This strategy suffers from the difficulties in controlling interfacial interactions during drying and limits the applications to biosensing, which often demands variable surface chemistry. This method approach utilizes a multi-layer "stacked coins" printing strategy to overcome these limitations. Major printing conditions, including droplet size and spacing, jetting frequency, and substrate temperature, have been optimized to achieve precise printing of complex 3D nanostructured patterns on a plain glass surface with a ~20 µm geometric resolution (FIG. 1C-1E). Such resolution is sufficient to print a majority of the existing micromixing architectures in microfluidic devices to leverage biosensing performance. In addition to the improved printing performance, a key advantage of this approach is its ability to directly print on an unmodified glass surface. Not only does this advance greatly simplify device manufacturing, but it also augments the adaptability to broad biosensing applications, which often demand variable surface chemistries. Compared to µCSA methods, the new printing-based process using a commercial-grade printer substantially enhanced the production scale, success rate, and robustness of device fabrication. Overall, this study is an essential step of the continuous efforts towards realizing industry-compatible manufacturing of 3D nano-engineered bioassay devices.

Building on the advance in chip fabrication, this study aimed to develop new bioanalytical capabilities to facilitate the progress of EV biology and clinical biomarker development. In contrast to existing microfluidic technologies that were focused on only molecular characterization of EVs, herein is reported a 3D nanoengineered lab-on-a-chip system that integrates an ultrasensitive proteolytic activity assay with quantitative molecular immunophenotyping to define the biofunctional signatures of circulating EVs associated with tumor invasion and metastasis. It was demonstrated that the activity assay vastly augments the sensitivity for detecting MMP14 on cell-derived EVs over the chip-based MMP14 immunoassay, conferring an approximately 10-fold lower LOD of ~$5\times10^2$ EVs $\mu L^{-1}$ (FIG. 2A-2D). Such improvement in sensitivity was also observed with the isogenic cell line models, mouse models, and clinical samples, which enhances the performance of sEV MMP-14 as a biomarker for cancer diagnosis and monitoring. Small sample consumption is another practical advantage of the EV-CLUE system, which can facilitate cancer research and clinical diagnostics. Mouse model is an indispensable tool for cancer research, and the ability to track tumor dynamics in vivo is critical to elucidating the processes and underlying mechanisms of tumor development and metastasis, as well as to assessing the effects of therapeutic agents. Current EV research involving longitudinal studies of mouse models often requires sacrificing a group of mice at each time point in order to collect sufficient sample quantity for standard bioassays. This approach causes some limitations, such as high cost and more importantly, inter-individual heterogeneity that can confound data analysis or even lead to misleading observations. The EV-CLUE system enables periodical measurements of minimally invasive volume of blood collected from individual mice to monitor tumor growth and metastasis in vivo. As a specific example, the blood test-based surveillance of human cancer cell line xenograft growing in each mouse was demonstrated through examining both total abundance and the MMP14+ subtype of human-derived sEVs in mouse plasma (FIGS. 4A-4E). With a spontaneous mouse metastasis model, this method enabled single-mouse longitudinal sEV analysis to detect large inter-individual heterogeneity and to capture unique trajectories of tumor development in individuals which could otherwise be masked by the ensemble measurement of different populations. Overall, these studies suggest this technology as a valuable tool to benefit animal studies of human diseases, especially for those challenging or expensive patient-derived xenografts (PDX) and transgenic models.

Figure 3B:
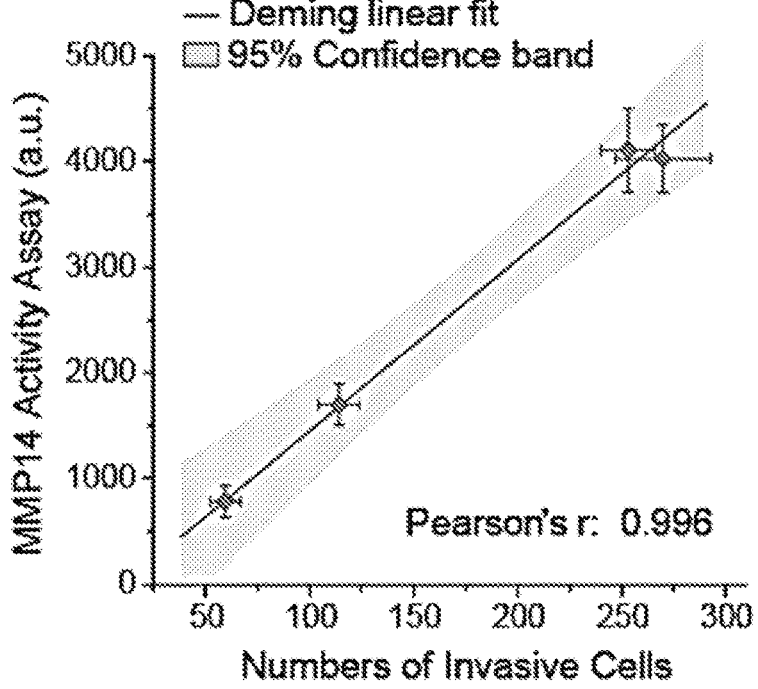

Enabled by the technical advance achieved herein, this work presents the first systematic assessment of clinical value of sEV MMP14 for tumor surveillance, using breast cancer as the disease model. EV-mediated transport of proteases is a newly discovered mechanism underlying tumor invasion and metastasis. There is evidence of EVs as a major route for cellular secretion of membrane-type metalloproteases, predominantly MMP14, into the extracellular space to mediate diverse proteolytic activities of cells. It was shown that knockdown of MMP14 expression, inhibition of MMP14 proteolytic activity, or inhibition of exosome biogenesis resulted in largely decreased activity of cancer cells, e.g., MDA-MB-231 cells, to degrade ECM. Consistently, among three major membrane-type MMPs that have been previously reported in breast cancer cell lines and tissues, considerable expression of MMP14 was detected, as opposed to MMP15 and MMP16 that are virtually indiscernible, on the purified EVs of various breast cancer cell lines (FIG. 3A). The assay detected activated MMP14 on these breast cancer cell-derived EVs, which agrees with the previous observation of EV-bound MMP14 being able to activate pro-MMPs and to degrade matrices. Furthermore, the studies of the MMP14 knockdown and HuR KO cells support the possible contributions of sEV MMP14 to cell invasion and its potential as an indicative biomarker of tumor progression and metastasis (FIGS. 3A-3B).

The molecular mechanisms governing activation and EV-mediated trafficking of MMP14 remain largely unknown. A general picture of this process involves endocytic internalization of membrane MMPs, conversion into functionally active forms, recycling back to plasma membrane or packing into intraluminal vesicles, and secretion as EVs. Growing evidence has shown that the traffic of MMP14 is controlled by diverse regulatory pathways and molecular machineries that may be differently programmed in tumor cells to drive ECM degradation and cell invasion depending on their pathological conditions and oncogenic stimuli. For instance, the vesicular SNARE (v-SNARE) protein family is a key component in the core machinery controlling intracellular trafficking and membrane fusion. The late endosomal v-SNARE, vesicle-associated membrane protein-7 (VAMP7), along with a subset of Rab GTPases (e.g., Rab27a and Rab5a), were found to form regulatory circuitries for spatially confined delivery of M1V1P14, which is crucial to the formation and function of invadopodia, membrane structures formed by invasive cells to protrude into ECM. Providing key docking sites for multivesicular bodies (MVB), invadopodia enhances secretion of MMP14-enriched exosomes that not only supports invadopodia formation but also promotes pericellular proteolysis of ECM to drive tumor progression and metastasis. In addition to the exosome biogenesis-associated routes, another v-SNARE, VAMP-3, has been recognized as a regulator for specified sorting and delivery of endosomal MMP14 into shedding microvesicles at the plasma membrane to support cancer cell invasion. VAMP3-mediated MMP14 exocytosis was found to be regulated by WDFY2, a protein involved in the early endocytic pathway. WDFY2 knockout leads to enhanced secretion of MMP14+ vesicles, promoted ECM degradation, and cell invasion. Differential dysregulation of these regulators, such as Rab5 overexpression and WDFY2 loss, are often implicated in human cancers, reinforcing the diverse and dynamic nature of the regulatory circuitries of MMP14 trafficking during oncogenic transformation. In this case, while it appeared that MMP14 is not a direct target of HuR, the KO of HuR downregulated EV trafficking of MMP14. Such HuR-regulated EV transport of MMP14 might constitute a component of the HuR-dependent regulatory network that promotes tumor development and metastasis. While the mechanism underlying the HuR-mediated regulation of EV MMP14 is still under investigation, which is beyond the scope of this Example, the in vitro results resonate with the existing evidence that suggests MMP14-enriched EVs as a functional indicator of tumor invasion and metastasis. This is further supported by the in vivo studies of experimental and spontaneous metastasis mouse models of breast cancer (FIGS. 4A-4E and FIGS. 5A-5D).

While previous mechanistic studies have shown biomedical significance of MMP14-mediated function of EVs, mostly using cell lines and animal models, its clinical value remains largely undetermined. To this end, the feasibility of probing sEV MMP14 for diagnosis and staging of breast cancer was assessed using clinical plasma specimen (FIGS. 6A-6D and FIGS. 7A-7D). Breast cancer is the most prevalent malignancy and the leading cause of cancer-related death in women. Five-year survival rate for women with localized breast cancer (Stage 0 to IIa) is 99% and drops down to 85% and 27% for women with regional lymph nodes metastases (Stage IIb and III) or distant metastases (Stage IV), respectively. ~25% of cases are diagnosed with in situ breast cancer, of which ~81% are DCIS. If not timely diagnosed and treated, 20-50% of these in situ cases will progress to invasive breast cancer and even with distant metastases. However, molecular mechanisms underlying early-stage progression in breast cancer is still elusive. Prior studies have suggested that the genetic alternations driving potential invasion may already occur at the earlier stage and the transcriptomic profiles were virtually indistinguishable among the distinct stages of progression. Since there are no effective markers to predict the risk or detect progression to invasive lesions, it remains challenging to accurately stratify DCIS lesions to improve treatment and eliminate unnecessary overtreatments. Thus, more informative and robust markers are pressingly needed to improve clinical management of breast cancer.

Figure 7D:
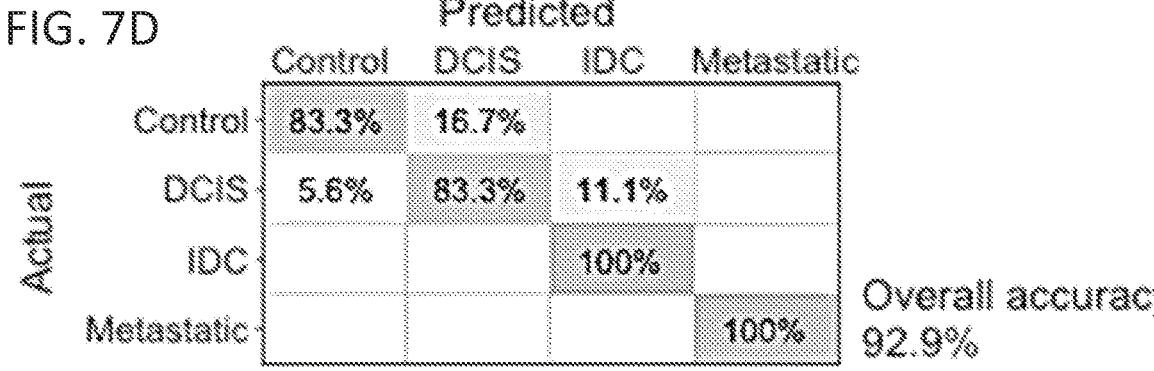

With two independent cohorts, it was shown that the plasma concentration and proteolytic activity of MMP14-positive sEVs can be used to detect the patient group (stage 0-III) against the control group, with the activity assay yielding the best diagnostic performance (AUC=0.977 for the training cohort and 0.986 for the validation cohort). Moreover, the sEV MMP14 expression and activity appeared to correlate with the progressive disease stages (FIGS. 6B and 7B), indicating the possibility for longitudinal surveillance of the progression and spread of breast carcinomas. The feasibility of these markers for differentiating non-cancer controls or in situ carcinoma from invasive and locally advanced cases was also demonstrated, which is the first major stratification of breast cancer types to guide clinical treatment. To further enhance the performance of this method for breast cancer diagnosis and stratification, discriminant analysis of the training cohort (n=30) was performed to derive a discriminant function model, which was then tested for classifying the patients in the validation cohort (n=70) without known a priori disease state. Combining three sEV parameters tested (i.e., total concentration and MMP14 expression and activity), a high overall accuracy of 92.9% (95% CI, 84.1-97.6%) was obtained for classifying all four groups in the validation cohort, and the sensitivity and specificity were 83.3% and 96.2% for identifying DCIS, 100% and 96.0% for non-metastatic IDC, and 100% and 100% for regionally metastatic patients, respectively (FIG. 7D). Overall, the clinical specimen analysis, combined with the in vitro cell line and in vivo mouse model studies, should have demonstrated the feasibility of the MMP14-targeted molecular and functional sEV phenotyping for predicting invasive potential, detecting early progression or metastasis with high sensitivity and specificity, and ultimately, informing individualized treatment of breast cancer.

The current study represents a feasibility study to evaluate the potential clinical utilities of the EV-CLUE system based on sEV MMP14 in cancer diagnosis and monitoring. This technology may be limited in detecting pre-cancerous and pre-EMT conditions due to the low abundance of tumor-derived EVs available in blood and the limited diagnostic performance of single biomarkers. The integrated and expandable multi-channel device could be multiplexed to analyze a number of functional proteases implicated in tumor invasion and metastasis, such as soluble MMPs, heparanases, and tissue inhibitors of metalloproteinases (TIMPs), to develop sensitive and specific liquid biopsy-based biomarker panels. Blood derivatives (plasma and serum) have been the most commonly used specimens in the studies of EV biomarkers, due in part to their wide clinical availability. As the goal of this technology development is to enhance the system robustness and clinical adaptability, the current device was designed for the analysis of plasma rather than whole blood, which simplifies the chip design, fabrication, and operation procedures. The chip could be expanded for whole blood analysis because of its inherent amenability to multifunctional integration (FIG. 1A) and the availability of a variety of microfluidic modules for plasma extraction or direct EV isolation from whole blood. The widely used tail vein injection and orthotopic mammary fat pad models provide a relevant means to assess and validate the technology to monitor tumor invasion and remote metastasis, despite their biological/clinical limitations. More in-depth studies, such as mechanistic and biomarker studies focused on DCIS-derived local tumor progression, will benefit from other mouse models of breast cancer that could closely recapitulate the biology of tumorigenesis and metastasis, including the intraductal injection and PDX models. Moving the sEV MMP14-based technology towards clinical applications will be benefited by rigorous clinical validation with much larger cohorts or long-term longitudinal studies of the development of high-risk in situ breast carcinomas into invasive or metastatic lesions. The amenability of the ink-jet printing technique developed here to robust and scalable device manufacturing will greatly facilitate such large-scale translational and clinical studies. For long-term studies, the applications of the EV-CLUE system can be expanded in different aspects of cancer medicine. For instance, analysis of MMP14-mediated sEV functions might also be expanded to assess treatment efficacy and to predict disease relapse.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A method for inkjet printing an object, the method comprising:
   (a) depositing a first droplet of an ink composition comprising particles dispersed in a liquid phase onto a surface of a substrate at first location and evaporating the liquid phase from the deposited first droplet to form a first ring structure on the surface at the first location, the first ring structure comprising the particles;
   (b) depositing a second droplet of the ink composition onto the surface at a second location laterally offset from the first location by a droplet spacing value and evaporating the liquid phase from the deposited second droplet to form a second ring structure on the surface at the second location, the second ring structure comprising the particles, wherein the second ring structure is offset from, and partially overlap s with, the first ring structure; and
   (c) repeating step (b) one or more additional times with one or more additional droplets to form a first layer of offset and partially overlapping ring structures on the surface of the substrate, the first layer comprising the first and second ring structures and one or more additional ring structures formed from the one or more additional droplets, thereby forming an object.

2. The method of claim 1, further comprising repeating steps (a), (b), and (c) one or more additional times to form one or more additional layers of offset and partially overlapping ring structures on the first layer.

3. The method of claim 2, further comprising forming an array of objects distributed across the surface of the substrate, each object in the array formed by carrying out steps (a), (b), and (c) and repeating steps (a), (b), and (c) one or more additional times.

4. The method of claim 1, wherein the droplet spacing value is in a range of from 2 μm to 10 μm.

5. The method of claim 1, wherein the ink composition is a colloidal suspension.

6. The method of claim 1, wherein the particles comprise silica particles, carbon particles, polystyrene particles, and combinations thereof.

7. The method of claim 1, wherein the particles are spherical.

8. The method of claim 7, wherein the particles have an average diameter in a range of from 100 nm to 5 μm.

9. The method of claim 1, wherein the substrate is an unmodified substrate.

10. The method of claim 1, wherein the ink composition is free of a surface tension modifier.

11. The method of claim 1, further comprising functionalizing the formed object so that the object is capable of capturing a target species.

12. The method of claim 11, wherein the object is functionalized with an antibody specific to an exosome.

13. The method of claim 12, wherein the antibody is anti-CD81 monoclonal antibody.

14. The method of claim 1, wherein each of the first ring structure, the second ring structure, and the additional ring structures have a circular shape and define an aperture through which at least some of the surface of the substrate is exposed.

* * * * *